United States Patent
Yamaguchi et al.

(10) Patent No.: US 9,403,159 B2
(45) Date of Patent: Aug. 2, 2016

(54) DEHYDROGENATION CATALYST, AND CARBONYL COMPOUND AND HYDROGEN PRODUCTION METHOD USING SAID CATALYST

(71) Applicant: Kanto Kagaku Kabushiki Kaisha, Tokyo (JP)

(72) Inventors: Ryohei Yamaguchi, Kyoto (JP); Ken-ichi Fujita, Kyoto (JP)

(73) Assignee: Kanto Kagaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/380,088

(22) PCT Filed: Feb. 22, 2013

(86) PCT No.: PCT/JP2013/054622
§ 371 (c)(1),
(2) Date: Aug. 21, 2014

(87) PCT Pub. No.: WO2013/125712
PCT Pub. Date: Aug. 29, 2013

(65) Prior Publication Data
US 2015/0086473 A1  Mar. 26, 2015
US 2016/0008801 A9  Jan. 14, 2016

(30) Foreign Application Priority Data

Feb. 23, 2012 (WO) .................. PCT/JP2012/054474

(51) Int. Cl.
| | |
|---|---|
| *B01J 31/22* | (2006.01) |
| *C01B 3/32* | (2006.01) |
| *C01B 3/06* | (2006.01) |
| *C07C 45/00* | (2006.01) |
| *C07F 17/02* | (2006.01) |
| *C01B 3/00* | (2006.01) |
| *C01B 3/22* | (2006.01) |

(52) U.S. Cl.
CPC ........... *B01J 31/2295* (2013.01); *C01B 3/0015* (2013.01); *C01B 3/06* (2013.01); *C01B 3/22* (2013.01); *C01B 3/326* (2013.01); *C07C 45/002* (2013.01); *C07F 17/02* (2013.01); *B01J 2231/766* (2013.01); *B01J 2531/827* (2013.01); *C01B 2203/0227* (2013.01); *C01B 2203/0277* (2013.01); *C01B 2203/1041* (2013.01); *C01B 2203/1205* (2013.01); *C01B 2203/1211* (2013.01); *C01B 2203/1217* (2013.01); *Y02E 60/328* (2013.01); *Y02E 60/36* (2013.01); *Y02P 20/132* (2015.11)

(58) Field of Classification Search
None
See application file for complete search history.

(56) References Cited

U.S. PATENT DOCUMENTS

2009/0124806 A1  5/2009  Iwabuchi et al.
2010/0034733 A1  2/2010  Fukuzumi et al.

FOREIGN PATENT DOCUMENTS

| CN | 101891147 A | 11/2010 |
|---|---|---|
| JP | 2009-078200 A | 4/2009 |
| JP | 2009-114143 A | 5/2009 |
| JP | 4572393 B2 | 11/2010 |

OTHER PUBLICATIONS

Anelli et al., Fast and selective oxidation of primary alcohols to aldehydes or to carboxylic acids and of secondary alcohols to ketones mediated by oxoammonium salts under two-phase conditions. J Org Chem. 1987;52(12):2559-62.
Choi et al., Heterogeneous Shvo-type ruthenium catalyst: dehydrogenation of alcohols without hydrogen acceptors. Tetrahedron Letters. Jun. 7, 2004;45(24): 4607-10.
Fujita et al., Dehydrogenative oxidation of primary and secondary alcohols catalyzed by a Cp*Ir complex having a functional C,N-chelate ligand. Org Lett. May 6, 2011;13(9):2278-81. doi: 10.1021/012005424. Epub Apr. 7, 2011.
Fujita et al., Ligand-promoted dehydrogenation of alcohols catalyzed by Cp*Ir complexes. A new catalytic system for oxidant-free oxidation of alcohols. Org Lett. Jan. 4, 2007;9(1):109-11.
Junge et al., Novel improved ruthenium catalysts for the generation of hydrogen from alcohols. Chem Commun (Camb). Feb. 7, 2007;(5):522-4. Epub Oct. 31, 2006. Erratum in: Chem Commun (Camb). Feb. 7, 2007;(5):530.
Junge et al., Ruthenium-catalyzed generation of hydrogen from isopropanol. Tetrahedron Letters. Feb. 7, 2005; 46(6):1031-4.
Kawahara et al., Dehydrogenative oxidation of alcohols in aqueous media using water-soluble and reusable Cp*Ir catalysts bearing afunctional bipyridine ligand. J Am Chem Soc. Feb. 29, 2012;134(8):3643-6. doi: 10.1021/ja210857z. Epub Feb. 16, 2012.
Kawahara et al., Dehydrogenative oxidation of primary and secondary alcohols in aqueous media catalyzed by novel water-soluble Cp*Ir complexes. 58th symposium on Organometallic Chemistry proceeding. Aug. 23, 2011.
Noyori et al., Green oxidation with aqueous hydrogen peroxide. Chem Commun (Camb). Aug. 21, 2003;(16):1977-86.

(Continued)

*Primary Examiner* — Yun Qian
(74) *Attorney, Agent, or Firm* — Wolf, Greenfield & Sacks, P.C.

(57) ABSTRACT

Objects of the present invention are to provide a novel dehydrogenation reaction catalyst, to provide a method that can produce a ketone, an aldehyde, and a carboxylic acid with high efficiency from an alcohol, and to provide a method for efficiently producing hydrogen from an alcohol, formic acid, or a formate, and they are accomplished by a catalyst containing an organometallic compound of Formula (1).

(1)

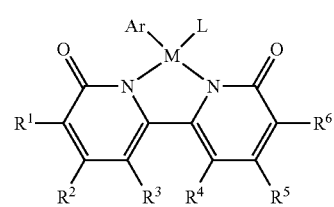

10 Claims, No Drawings

(56) References Cited

OTHER PUBLICATIONS

Tanaka et al., Dehydrogenation and hydrogenation reactions of nitrogen heterocycles catalyzed by novel Cp*Ir complexes having functional bipyridine ligands. 58th symposium on Organometallic Chemistry proceeding. Aug. 23, 2011.

Van Buijtenen et al., Dinuclear Ruthenium Complexes Bearing Dicarboxylate and Phosphine Ligands. Acceptorless Catalytic Dehydrogenation of 1-Phenylethanol. Organometallics. 2006; 25(4):873-81.

Zhang et al., Facile conversion of alcohols into esters and dihydrogen catalyzed by new ruthenium complexes. J Am Chem Soc. Aug. 10, 2005;127(31):10840-1. Erratum in: J Am Chem Soc. Sep. 7, 2005;127(35):12429.

International Preliminary Report on Patentability for International Application No. PCT/JP2013/054622 mailed Sep. 4, 2014.

Himeda, Efficient Catalytic Hydrogenation of $CO_2$ and Decomposition of Formic Acid Using Catalysts with 4,4'-Dihydroxy-2,2'-bipyridien. The $90^{th}$ Annual Meeting of the Chemical Society of Japan in Spring Koen Yokoshu, Mar. 12, 2010, II, p. 161 (2B2-42).

Kawahara et al., Dehydrogenative Oxidation of Alcohols in Aqueous Media Catalyzed by Novel Water-Soluble Cp* Iridium Complexes. The $91^{st}$ Annual Meeting of the Chemical Society of Japan in Spring Koen Yokoshu, Mar. 11, 2011, IV, p. 1349 (4C5-48).

Tanaka et al., Synthesis of Novel Cp*Ir Complexes Having Functional Bipyridine Ligands and Their Catalytic Activities in Dehydrogenation of Nitrogen Heterocycles. The $91^{st}$ Annual Meeting of the Chemical Society of Japan in Spring Koen Yokoshu, Mar. 11, 2011, IV, p. 1348 (4C5-47).

DEHYDROGENATION CATALYST, AND CARBONYL COMPOUND AND HYDROGEN PRODUCTION METHOD USING SAID CATALYST

RELATED APPLICATION

This application is a national stage filing under 35 U.S.C. §371 of PCT International application PCT/JP2013/054622, filed Feb. 22, 2013.

TECHNICAL FIELD

The present invention relates to a dehydrogenation reaction catalyst containing an organometallic complex having a nitrogen-containing ligand. The present invention also relates to a dehydrogenation method employing the organometallic complex as a catalyst, a method for producing a carbonyl compound by a dehydrogenation reaction of an alcohol, and a method for producing hydrogen by a dehydrogenation reaction of an alcohol, formic acid, or a formate. Furthermore, the present invention relates to a novel organometallic complex having a nitrogen-containing ligand.

BACKGROUND ART

A dehydrogenation reaction of a hydrogen-containing organic compound is one of the most important reactions in organic synthesis, and is a reaction that has high utility value in industry. For example, a conversion reaction involving a dehydrogenation reaction (oxidation reaction) of an alcohol into a carbonyl compound such as an aldehyde, a ketone, or a carboxylic acid plays an important role in the production of organic compounds used in many fields such as pharmaceuticals, agrochemicals, food, fragrances, and materials, or starting materials therefor. Furthermore, a method for producing hydrogen by a dehydrogenation reaction of an alcohol, formic acid, or a formate is a technique that has been attracting attention as a technique for supplying and storing hydrogen for a fuel cell.

Synthesis of a carbonyl compound by an oxidative dehydrogenation reaction of an alcohol is one of the most important functional group conversions in organic syntheses for obtaining intermediates for pharmaceuticals, agrochemicals, fragrances, etc., and in the past a large number of excellent oxidizing agents and oxidation reactions have been developed. For example, as a stoichiometric oxidizing reagent, an oxidation method using a heavy metal oxidizing agent (potassium permanganate, bichromic acid or a salt thereof, chromium trioxide, etc.), a DMSO oxidation method (Swern oxidation, etc.), etc. are known. It is difficult to use these oxidizing agents and oxidation methods industrially in terms of safety and environmental friendliness due to the production of large amounts of highly toxic waste material by-products and the occurrence of bad odors.

On the other hand, from the viewpoint of environmentally friendly green chemistry, catalytic oxidation reactions of alcohols using a co-oxidizing agent such as hydrogen peroxide, acetone, or molecular oxygen have been developed. However, a reaction using a co-oxidizing agent has the problems that depending on the type of co-oxidizing agent, the reaction becomes complicated, and the substrates to which it can be applied are limited, and there is still room for improvement from the viewpoint of design of a catalytic reaction based on atom efficiency.

Thus, from a process chemistry viewpoint it is very important to develop a catalytic oxidation reaction of an alcohol without using a co-oxidizing agent, that is, a catalytic oxidative dehydrogenation reaction. In recent years, such reactions have been reported one after another and, for example, oxidative dehydrogenation reactions using ruthenium catalysts (Non-Patent Documents 1 to 5) or iridium catalysts (Non-Patent Documents 6 and 7) have been reported. However, there are problems in terms of industrial application, in that these reactions are carried out at a relatively high temperature, a reaction requiring basic conditions cannot be applied to a substrate that is unstable toward a base, and the amount of catalyst is relatively large.

Furthermore, Non-Patent Document 8 reports a dehydrogenative oxidation reaction of an alcohol using a cationic iridium complex; the reaction is carried out in aqueous solvent under reflux conditions, but while taking into consideration safety and economy it is desirable for it to be carried out at a lower temperature. Moreover, in this reaction, since the cationic iridium complex itself exhibits acidity, it is not suitable for a reaction of a substrate that is susceptible to decomposition in an acidic state. Furthermore, Non-Patent Document 9 reports a catalytic dehydrogenation reaction of a cyclic amine (2,6-dimethyldecahydro-1,5-naphthyridine) using a neutral iridium complex, but the use of an alcohol in a catalytic dehydrogenation reaction has not been tried.

From the above, there has been a desire for the development of a catalytic dehydrogenation reaction of an alcohol that can be carried out with a small amount of catalyst at a relatively low temperature.

Furthermore, an aldehyde is prepared by an oxidation reaction of a primary alcohol, and the aldehyde is further oxidized to give the corresponding carboxylic acid; being able to make this proceed as a one pot reaction is very important from the viewpoint of process chemistry. As a stoichiometric oxidizing agent that can be used for this purpose, potassium permanganate ($KMnO_4$), Jones reagent, and pyridinium dichromate (PDC) are known, but it is difficult to carry out these methods industrially in terms of economy and safety such as a large amount of heavy metal being used and a highly toxic compound being produced as a by-product.

As catalytic methods, oxidation methods using ruthenium tetroxide, and TEMPO (Non-Patent Document 10) are known, but due to the conditions being relatively severe it is difficult to apply them to compounds having a large number of functional groups, and due to the use of a co-oxidizing agent there is still room for improvement from the viewpoint of design of a catalytic reaction based on atom efficiency. A method using sodium tungstate (Non-Patent Document 11) as a catalyst is a reaction that is accompanied by danger due to the use of a high concentration of aqueous hydrogen peroxide. 1-Me-AZADO oxidation (Patent Document 1), which has improved the defect of TEMPO oxidation, has also been developed, but since this method also requires a large amount of co-oxidizing agent, there has been a desire for the development of a catalyst that can reduce the environmental burden.

As described above, there has been a desire for the development of an oxidative dehydrogenation reaction that will take a primary alcohol to a carboxylic acid via an aldehyde and that will progress with a small amount of catalyst without using a co-oxidizing agent.

On the other hand, hydrogen ($H_2$) has conventionally been utilized in various industrial fields, such as for petroleum purification or as a chemical starting material, and in recent years it has received attention as fuel for a fuel cell. However, since hydrogen is gaseous at room temperature, highly reactive, and susceptible to ignition in air, the stable supply and storage of hydrogen is an important issue in the development of fuel cells. For example, as methods for storing hydrogen there are known a method in which it is stored as a compressed gas, a method in which hydrogen gas is liquefied and stored in the form of liquid hydrogen, and a method in which hydrogen is taken into a hydrogen absorbing alloy and stored. However, these methods have the problem that the amount of hydrogen stored per unit weight of storage medium is small and, in addition, there are problems with cost, safety, and handling.

In order to solve these problems, a method for storing hydrogen in the form of a substance other than $H_2$ could be considered. For example, formic acid ($HCO_2H$) is known to generate hydrogen ($H_2$) and carbon dioxide ($CO_2$) when strongly heated. It is possible by utilizing this to store hydrogen in the form of formic acid, which is a stable substance, and to stably supply hydrogen by appropriately heating formic acid and generating hydrogen. However, since it is necessary to carry out a thermal decomposition reaction of formic acid at a high temperature, there has been a desire for the development of a catalyst that can generate hydrogen from formic acid with high efficiency under mild conditions.

As catalysts for the decomposition of formic acid, examples using a metal complex have already been reported. For example, a polynuclear metal complex containing iridium and ruthenium has been reported in Patent Document 2, but due to the use of two types of transition metals the production cost is high. Furthermore, a decomposition reaction of formic acid using a rhodium complex has been reported in Patent Document 3, but the rhodium complexes in the examples are limited to cationic aquo complexes having a bipyridyl-based ligand, and the amount of catalyst used is about 1 mol %, which cannot necessarily be said to be efficient.

From the above, there has been a desire for the development of a catalyst for a decomposition reaction of formic acid or a formate that has high reactivity with a small amount of catalyst under mild conditions.

PRIOR ART DOCUMENTS

Patent Documents

[Patent Document 1] JP, A, 2009-114143
[Patent Document 2] JP, 4572393
[Patent Document 3] JP, A, 2009-78200

Non-Patent Documents

[Non-Patent Document 1] J. Ho Choi, N. Kim, Y. J. Shin, J. H. Park and J. Park, Tetrahedron Lett., 2004, 45, 4607-4610.
[Non-Patent Document 2] H. Junge and M. Beller, Tetrahedron Lett., 2005, 46, 1031-1034.
[Non-Patent Document 3] J. Zhang, G. Leitus, Y. Ben-David and D. Milstein, J. Am. Chem. Soc., 2005, 127, 10840-10841.
[Non-Patent Document 4] J. van Buijtenen, J. Meuldijk et al., Organometallics, 2006, 25, 873-881.
[Non-Patent Document 5] H. Junge, B. Loges, and M. Beller, Chem. Commun., 2007, 522-524.
[Non-Patent Document 6] K. Fujita, N. Tanino and R. Yamaguchi, Org. Lett., 2007, 9 (1), 109-111.
[Non-Patent Document 7] K. Fujita, T. Yoshida, Y. Imori and R. Yamaguchi, Org. Lett., 2011, 13 (9), 2278-2281.
[Non-Patent Document 8] Ryoko Kawahara, Kenichi Fujita, and Ryohei Yamaguchi, 'Dehydrogenative oxidation reaction of alcohols using a novel water-soluble Cp* iridium complex catalyst in aqueous solvent', Proceedings of 91st Spring Meeting of the Chemical Society of Japan, 11 Mar. 2011, Lecture Number 4C5-48
[Non-Patent Document 9] Yui Tanaka, Kenichi Fujita, and Ryohei Yamaguchi, 'Synthesis of a novel Cp* iridium complex having functional bipyridine-based ligand and catalytic dehydrogenation reaction of nitrogen-containing heterocycles', Proceedings of 91st Spring Meeting of the Chemical Society of Japan, 11 Mar. 2011, Lecture Number 4C5-47
[Non-Patent Document 10] Anelli. P. L, Biffi. C, Montanari. F and Quici. S, J. Org. Chem., 1987, 52, 2559-2562.
[Non-Patent Document 11] R. Noyori, M. Aoki and K. Sato, Chem. Commun., 2003, 1977.

SUMMARY OF THE INVENTION

Problems to be Solved by the Invention

It is an object of the present invention to provide a novel dehydrogenation reaction catalyst. It is another object of the present invention to provide a method that can produce a ketone, an aldehyde, and a carboxylic acid from an alcohol with high efficiency, and to provide a method for efficiently producing hydrogen from an alcohol, formic acid, or a formate.

Means for Solving the Problems

While carrying out an intensive investigation in order to accomplish the above objects, the present inventors have found that by the use of a catalyst containing a neutral organometallic compound containing a ligand having carbonyl oxygen and nitrogen, dehydrogenation reactions of an alcohol and formic acid or a formate progress smoothly; it has been found during further investigation that the catalytic efficiency and the reaction yield can be greatly improved by means of the novel complex and, furthermore, not only a dehydrogenation reaction but also interconversion by reversible dehydrogenation-hydrogenation can be quantitatively carried out repeatedly accompanied by the release and absorption of hydrogen, and the present invention has thus been accomplished.

Effects of the Invention

In accordance with the catalyst of the present invention, a dehydrogenation reaction of an alcohol and a decomposition reaction of formic acid or a formate can be achieved at high yield without requiring a co-oxidizing agent. Since the complex of the present invention is a neutral complex and exhibits high solubility in most of the usual organic solvents, solvents having various boiling points can be freely selected and used. It is also possible to select and use a solvent that easily dissolves a substrate. Furthermore, in accordance with the present invention, the decomposition reaction of formic acid or a formate can be carried out at a reaction temperature of 100° C. or below, which is very advantageous in industrial applications in terms of safety and economy.

Moreover, in accordance with the present invention, reversible dehydrogenation-hydrogenation interconversion can be carried out by the use of the same catalyst. That is, the catalyst of the present invention can be used if desired in both directions in the reaction of the reaction formula below.

Reaction formula (I)

[Formula 1]

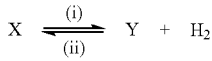

wherein
X is a hydrogen-containing compound or an oxygen-containing compound,
Y is a compound, corresponding to X, that is a carbonyl compound or an unsaturated bond-containing compound,
(i) is dehydrogenation, and
(ii) is hydrogenation.

In particular, the catalyst of the present invention containing a novel compound (complex) having an aquo ligand exhibits very high catalytic efficiency and reaction yield, and is a very useful catalyst.

MODES FOR CARRYING OUT THE INVENTION

That is, the present invention relates to the following.
[1] A method for dehydrogenating an oxygen-containing compound by the use of a catalyst containing an organometallic compound of Formula (1)

[Chem. 1]

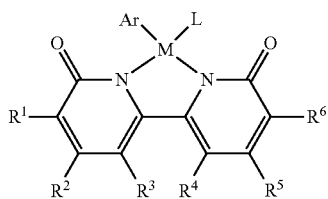

wherein
Ar is an optionally substituted benzene or an optionally substituted cyclopentadienyl group,
M is ruthenium, rhodium, or iridium,
$R^1$ to $R^6$ are mutually independently a hydrogen atom, a halogen atom, a nitro group, a cyano group, a hydroxy group, a sulfo group, a mercapto group, a carboxyl group, or a C1-10 alkyl group, C3-15 cycloalkyl group, C6-15 aryl group, C1-10 heterocyclyl group, C2-10 alkenyl group, C2-10 alkynyl group, C1-10 alkoxy group, C1-10 ester group, C1-10 fluoroalkyl group, C1-10 acyl group, C1-10 sulfonyl group, C1-10 amino group, C1-10 amide group, C1-10 sulfenyl group, or C1-10 silyl group in which one or more hydrogen atoms are optionally substituted,
$R^3$ and $R^4$ may be bonded to each other to form —CH=CH—, the Hs in the —CH=CH— are optionally substituted mutually independently by a halogen atom, a nitro group, a cyano group, a hydroxy group, a sulfo group, a mercapto group, a carboxyl group, or a C1-10 alkyl group, C3-15 cycloalkyl group, C6-15 aryl group, C1-10 heterocyclyl group, C2-10 alkenyl group, C2-10 alkynyl group, C1-10 alkoxy group, C1-10 ester group, C1-10 fluoroalkyl group, C1-10 acyl group, C1-10 sulfonyl group, C1-10 amino group, C1-10 amide group, C1-10 sulfenyl group, or C1-10 silyl group in which one or more hydrogen atoms are optionally substituted, and L is selected from the group consisting of a sulfoxide ligand, a nitrogen-containing aromatic ring ligand, an amine ligand, a phosphine ligand, an ether ligand, and an aquo ligand.
[2] The method according to [1], wherein the oxygen-containing compound is an alcohol.
[3] The method according to [1], wherein the oxygen-containing compound is formic acid or a formate.
[4] The method according to any one of [1] to [3], wherein L is an aquo ligand.
[5] The method according to any one of [1] to [4], wherein Ar is an optionally substituted cyclopentadienyl group, and M is iridium.
[6] A dehydrogenation catalyst containing an organometallic compound of Formula (1), wherein it is for use in the method according to any one of [1] to [5].
[7] A method for producing a carbonyl compound, wherein an alcohol is dehydrogenated by use of the dehydrogenation method according to any one of [1] to [5] to produce a corresponding carbonyl compound.
[8] The method according to [7], wherein the carbonyl compound is a ketone or an aldehyde.
[9] The method according to [7], wherein the alcohol is a primary alcohol, the carbonyl compound is a carboxylic acid, and a solvent containing water is used.
[10] A method for producing hydrogen, wherein hydrogen is prepared by dehydrogenation of an alcohol, a mixture containing an alcohol and water, formic acid, or a formate using the dehydrogenation method according to any one of [1] to [5].
[11] An organometallic compound of Formula (1)

[Chem. 2]

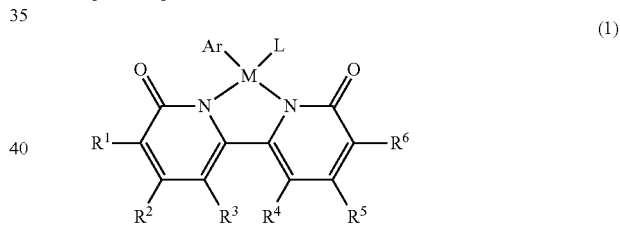

wherein,
Ar is an optionally substituted benzene or an optionally substituted cyclopentadienyl group,
M is ruthenium, rhodium, or iridium,
$R^1$ to $R^6$ are mutually independently a hydrogen atom, a halogen atom, a nitro group, a cyano group, a hydroxy group, a sulfo group, a mercapto group, a carboxyl group, or a C1-10 alkyl group, C3-15 cycloalkyl group, C6-15 aryl group, C1-10 heterocyclyl group, C2-10 alkenyl group, C2-10 alkynyl group, C1-10 alkoxy group, C1-10 ester group, C1-10 fluoroalkyl group, C1-10 acyl group, C1-10 sulfonyl group, C1-10 amino group, C1-10 amide group, C1-10 sulfenyl group, or C1-10 silyl group in which one or more hydrogen atoms are optionally substituted,
$R^3$ and $R^4$ may be bonded to each other to form —CH=CH—, the Hs in the —CH=CH— are optionally substituted mutually independently by a halogen atom, a nitro group, a cyano group, a hydroxy group, a sulfo group, a mercapto group, a carboxyl group, or a C1-10 alkyl group, C3-15 cycloalkyl group, C6-15 aryl group, C1-10 heterocyclyl group, C2-10 alkenyl group, C2-10 alkynyl group, C1-10 alkoxy group, C1-10 ester group, C1-10 fluoroalkyl group, C1-10 acyl group, C1-10 sulfonyl group, C1-10 amino group, C1-10 amide group, C1-10 sulfenyl group, or C1-10 silyl group in which one or more hydrogen atoms are optionally substituted, and L is an aquo ligand.

[12] The organometallic compound according to [11], wherein Ar is an optionally substituted cyclopentadienyl group, and M is iridium.

[13] An organometallic compound of Formula (2)

[Chem. 3]

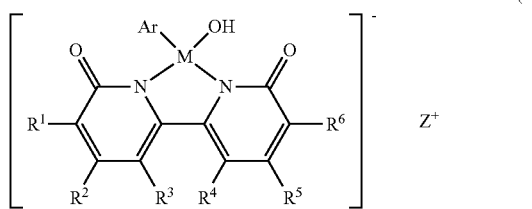

(2)

wherein

Ar is an optionally substituted benzene or an optionally substituted cyclopentadienyl group, M is ruthenium, rhodium, or iridium, $R^1$ to $R^6$ are mutually independently a hydrogen atom, a halogen atom, a nitro group, a cyano group, a hydroxy group, a sulfo group, a mercapto group, a carboxyl group, or a C1-10 alkyl group, C3-15 cycloalkyl group, C6-15 aryl group, C1-10 heterocyclyl group, C2-10 alkenyl group, C2-10 alkynyl group, C1-10 alkoxy group, C1-10 ester group, C1-10 fluoroalkyl group, C1-10 acyl group, C1-10 sulfonyl group, C1-10 amino group, C1-10 amide group, C1-10 sulfenyl group, or C1-10 silyl group in which one or more hydrogen atoms are optionally substituted, $R^3$ and $R^4$ may be bonded to each other to form —CH=CH—, the Hs in the —CH=CH— are optionally substituted mutually independently by a halogen atom, a nitro group, a cyano group, a hydroxy group, a sulfo group, a mercapto group, a carboxyl group, or a C1-10 alkyl group, C3-15 cycloalkyl group, C6-15 aryl group, C1-10 heterocyclyl group, C2-10 alkenyl group, C2-10 alkynyl group, C1-10 alkoxy group, C1-10 ester group, C1-10 fluoroalkyl group, C1-10 acyl group, C1-10 sulfonyl group, C1-10 amino group, C1-10 amide group, C1-10 sulfenyl group, or C1-10 silyl group in which one or more hydrogen atoms are optionally substituted, and Z is Na, Li, K, or Cs.

[14] The organometallic compound according to [13], wherein Ar is an optionally substituted cyclopentadienyl group, and M is iridium.

[15] A method for dehydrogenating an oxygen-containing compound by the use of a catalyst containing the organometallic compound according to [13] or [14].

[16] The method according to [15], wherein the oxygen-containing compound is an alcohol, formic acid, or a formate.

[17] A dehydrogenation catalyst containing the organometallic compound according to [13] or [14].

[18] A method for producing a carbonyl compound, wherein an alcohol is dehydrogenated by use of the dehydrogenation method according to [15] or [16] to produce a corresponding carbonyl compound.

[19] The method according to [18], wherein the carbonyl compound is a ketone or an aldehyde.

[20] The method according to [18], wherein the alcohol is a primary alcohol, the carbonyl compound is a carboxylic acid, and a solvent containing water is used.

[21] A method for producing hydrogen, wherein hydrogen is prepared by dehydrogenation of an alcohol, a mixture of an alcohol and water, formic acid, or a formate by use of the dehydrogenation method according to [16].

[22] A method for continuously producing hydrogen, the method including adding an alkaline compound to a mixture containing an alcohol and water, carrying out a dehydrogenation reaction in the presence of an organometallic compound of Formula (1) according to [1] and/or Formula (2) according to [13], and adding said mixture and said alkaline compound one or more times in the course of progress of dehydrogenation.

[23] A system for continuously producing hydrogen by use of the method according to [22], the system including a reaction vessel for carrying out a dehydrogenation reaction, a supply section for supplying the mixture and the alkaline compound, and a recovery section for recovering hydrogen produced.

One aspect of the present invention relates to a method for dehydrogenating an oxygen-containing compound using a catalyst containing a nitrogen-containing organometallic compound (organometallic complex) of Formula (1) below. The organometallic complex used in the present invention is not particularly limited as long as it is a metal complex containing a ligand containing carbonyl oxygen and nitrogen on bipyridine or phenanthroline, and is typically of Formula (1).

[Chem. 4]

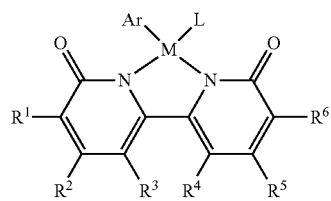

(1)

In Formula (1), Ar is typically a benzene or cyclopentadienyl group in which one or more hydrogen atoms are optionally substituted.

Specific examples of aromatic compounds in which one or more hydrogen atoms are optionally substituted include, but are not limited to, benzene, benzenes having an alkyl group such as toluene, o-, m- and p-xylene, o-, m- and p-cymene, 1,2,3-, 1,2,4- and 1,3,5-trimethylbenzene, 1,2,4,5-tetramethylbenzene, 1,2,3,4-tetramethylbenzene, 1,3,4,5-tetramethylbenzene, pentamethylbenzene, and hexamethylbenzene, benzenes having an unsaturated hydrocarbon group such as benzyl, vinyl, or allyl, and benzenes having a heteroatom such as a halogen atom, a hydroxy group, an alkoxy group, an ester group, or an amino group. The number of substituents on the benzene ring may be any of 1 to 6, and the position of substitution can be selected from any position. In terms of ease of synthesis of a complex, p-cymene, 1,3,5-trimethylbenzene, or hexamethylbenzene is preferable.

In the present invention, 'being optionally substituted' means optionally having any substituent; typical substituents include, but are not limited to, a C1-10 saturated or unsaturated hydrocarbon group, an aryl group, a heterocyclyl group, an alkoxy group, a fluoroalkyl group, an acyl group, an ester group, a hydroxy group, an amino group, an amide group, a carboxyl group, a sulfonyl group, a nitro group, a cyano group, a sulfenyl group, a sulfo group, a mercapto group, a silyl group, and a halogen group and, in particular, a C1-10 saturated or unsaturated hydrocarbon group, an aryl group, a heterocyclyl group, an alkoxy group, an acyl group, an ester group, a hydroxy group, an amino group, a sulfonyl group, a silyl group, and a halogen group.

Specific examples of the substituent include, but are not limited to, a methyl group, an ethyl group, an n-propyl group, an i-propyl group, a butyl group, a pentyl group, a hexyl group, a cyclohexylene group, an ethenyl group, a propenyl group, a butenyl group, a phenyl group, a toluyl group, a naphthyl group, a pyridyl group, a furanyl group, a methoxy group, an ethoxy group, a propoxy group, an acetyl group, a propanoyl group, a cyclohexanecarbonyl group, a benzoyl group, a methoxycarbonyl group, an ethoxycarbonyl group, a hydroxy group, a methylamino group, an ethylamino group, a dimethylamino group, a methylsulfonyl group, an ethylsulfonyl group, a methylsilyl group, a dimethylsilyl group, a fluoro group, a chloro group, and a trifluoromethyl group. In terms of ease of synthesis of a complex, a saturated or unsaturated hydrocarbon group is preferable, and a methyl group or an i-propyl group is more preferable.

Specific examples of the cyclopentadienyl group in which one or more hydrogen atoms are optionally substituted include, but are not limited to, a cyclopentadienyl group, a methylcyclopentadienyl group, an ethylcyclopentadienyl group, an isopropylcyclopentadienyl group, a phenylcyclopentadienyl group, a benzylcyclopentadienyl group, a 1,2-dimethylcyclopentadienyl group, a 1,3-dimethylcyclopentadienyl group, a 1,2,3-trimethylcyclopentadienyl group, a 1,2,4-trimethylcyclopentadienyl group, a 1,2,3,4-tetramethylcyclopentadienyl group, and a 1,2,3,4,5-pentamethylcyclopentadienyl group (Cp*). In terms of ease of synthesis of a complex, a 1,2,3,4,5-pentamethylcyclopentadienyl group (Cp*) is preferable.

M in Formula (1) is any of ruthenium, rhodium, and iridium. In terms of high catalytic activity, iridium is preferable.

$R^1$ to $R^6$ in Formula (1) are typically mutually independently a hydrogen atom, a halogen atom, a nitro group, a cyano group, a hydroxy group, a sulfo group, a mercapto group, a carboxyl group, or a C1-10 alkyl group, C3-15 cycloalkyl group, C6-15 aryl group, C1-10 heterocyclyl group, C2-10 alkenyl group, C2-10 alkynyl group, C1-10 alkoxy group, C1-10 ester group, C1-10 fluoroalkyl group, C1-10 acyl group, C1-10 sulfonyl group, C1-10 amino group, C1-10 amide group, C1-10 sulfenyl group, or C1-10 silyl group in which one or more hydrogen atoms are optionally substituted, $R^3$ and $R^4$ may be bonded to each other to form —CH=CH—, and the Hs in —CH=CH— are optionally substituted mutually independently by a halogen atom, a nitro group, a cyano group, a hydroxy group, a sulfo group, a mercapto group, a carboxyl group, or a C1-10 alkyl group, C3-15 cycloalkyl group, C6-15 aryl group, C1-10 heterocyclyl group, C2-10 alkenyl group, C2-10 alkynyl group, C1-10 alkoxy group, C1-10 ester group, C1-10 fluoroalkyl group, C1-10 acyl group, C1-10 sulfonyl group, C1-10 amino group, C1-10 amide group, C1-10 sulfenyl group, or C1-10 silyl group in which one or more hydrogen atoms are optionally substituted.

Specific examples of $R^1$ to $R^6$ include, but are not limited to, a hydrogen atom, a fluoro group, a chloro group, a bromo group, an iodo group, a trifluoromethyl group, a nitro group, a cyano group, a hydroxy group, a sulfo group, a mercapto group, a carboxyl group, a methoxy group, an ethoxy group, an n-propoxy group, an iso-propoxy group, a tert-butoxy group, a dimethylamino group, a methyl group, an ethyl group, an n-propyl group, an i-propyl group, a tert-butyl group, an isobutyl group, a benzyl group, a cyclohexyl group, a phenyl group, a vinyl group, a pyridyl group, an ethynyl group, an ester bond-containing group, an acetyl group, a methanesulfonyl group, an ethanesulfonyl group, a p-toluenesulfonyl group, a trifluoromethanesulfonyl group, a methylsilyl group, a dimethylsilyl group, and a trimethylsilyl group and so on. In terms of high catalytic activity and reaction yield, a hydrogen atom, a methyl group, an ethyl group, an isopropyl group, a tert-butyl group, an isobutyl group, a benzyl group, a phenyl group, a 4-methoxyphenyl group, or a 4-(dimethylamino)phenyl group is preferable.

L in Formula (1) is typically selected from the group consisting of a sulfoxide ligand, a nitrogen-containing aromatic ring ligand, an amine ligand, a phosphine ligand, an ether ligand, and an aquo ligand.

Specific examples thereof include, but are not limited to, DMSO, diphenylsulfoxide, and methylphenylsulfoxide as the sulfoxide ligand, pyridine, picoline, lutidine, 3-chloropyridine, and 4-chloropyridine as the nitrogen-containing aromatic ring ligand, aniline, toluidine, and anisidine as the amine ligand, triphenylphosphine, trimethylphosphine, triethylphosphine, tributylphosphine, tri-tert-butylphosphine, tricyclohexylphosphine, and triethoxyphosphine as the phosphine ligand, and dimethyl ether, diethyl ether, diisopropyl ether, cyclopentyl methyl ether, methyl tert-butyl ether, tetrahydrofuran, 2-methyltetrahydrofuran, and anisole as the ether ligand.

L is preferably a dimethylsulfoxide ligand (dmso), a pyridine ligand (pyridine), an aniline ligand (aniline), or an aquo ligand, and is particularly preferably an aquo ligand in terms of very high catalytic efficiency and reaction yield.

In the present invention, a preferred organometallic complex is a complex of Formula (1), wherein Ar being an optionally substituted cyclopentadienyl group, M being iridium, and L being a dimethylsulfoxide ligand (dmso), a pyridine ligand (pyridine), an aniline ligand (aniline), or an aquo ligand. Since the organometallic complex of the present invention is a neutral complex, it exhibits high solubility in most of the usual organic solvents, and solvents having various boiling points may be freely selected and used. It is also possible to select and use a solvent that easily dissolves a substrate.

From the viewpoint of catalytic efficiency and reaction yield, in particular, an organometallic complex of Formula (1), wherein Ar is an optionally substituted cyclopentadienyl group, M is iridium, and L is an aquo ligand, that is, an aquo complex, is preferable. Although the reason why this aquo complex exhibits very high catalytic efficiency and reaction yield is not necessarily clear, it is surmised that an aquo ligand easily dissociates and a coordinatively-unsaturated active species is easily generated.

In the present invention, the oxygen-containing compound may be a compound containing oxygen and hydrogen, and examples thereof include, but are not limited to, an alcohol, formic acid, and a formate.

The alcohol may be a primary alcohol or a secondary alcohol but is not limited thereto.

The primary alcohol is a compound typically of Formula (3)

[Chem. 5]

$$R^7-CH_2OH \qquad (3)$$

wherein $R^7$ denotes a hydrogen atom or an optionally substituted C5 to C15 aromatic monocyclic or polycyclic hydrocarbon group, C1 to C15 heteroatom-containing heteromonocyclic or polycyclic group, or C1 to C25 saturated or unsaturated chain-form or cyclic hydrocarbon group.

The substituent in this case may be selected as appropriate from for example a hydrogen atom, a halogen atom, a nitro group, a cyano group, a hydroxy group, a sulfo group, a mercapto group, a carboxyl group, or a C1-10 alkyl group, C3-15 cycloalkyl group, C5 to 15 aryl group, C1-15 heterocyclyl group, C2-10 alkenyl group, C2-10 alkynyl group, C1-10 alkoxy group, C1-10 ester group, C1-10 fluoroalkyl group, C1-10 acyl group, C1-10 sulfonyl group, C1-10 amino group, C1-10 amide group, C1-10 sulfenyl group, or C1-10 silyl group in which one or more hydrogen atoms are optionally substituted.

Specific examples of $R^7$ include a hydrogen atom, an aromatic monocyclic or polycyclic group such as a phenyl group, 2-methylphenyl, 2-ethylphenyl, 2-isopropylphenyl, 2-tert-butylphenyl, 2-methoxyphenyl, 2-chlorophenyl, 2-vinylphenyl, 3-methylphenyl, 3-ethylphenyl, 3-isopropylphenyl, 3-methoxyphenyl, 3-chlorophenyl, 3-vinylphenyl, 4-methylphenyl, 4-ethylphenyl, 4-isopropylphenyl, 4-tert-butylphenyl, 4-vinylphenyl, cumenyl, mesityl, xylyl, 1-naphthyl, 2-naphthyl, anthryl, phenanthryl, or indenyl group, a heteromonocyclic or polycyclic group such as thienyl, furyl, pyranyl, xanthenyl, pyridyl, pyrrolyl, imidazolinyl, indolyl, carbazoyl, or Phenanthrolinyl, an alkyl group such as methyl, ethyl, propyl, butyl, pentyl, hexyl, or heptyl, a cycloalkyl group such as cyclopropyl, cyclobutyl, cyclopentyl, cyclohexyl, or 2-adamantyl, an unsaturated hydrocarbon group such as benzyl, vinyl, or aryl, and a ferrocenyl group.

The secondary alcohol is typically of Formula (4)

[Chem. 6]

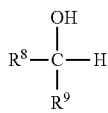

(4)

wherein $R^8$ and $R^9$ denote identical or different optionally substituted C5 to C15 aromatic monocyclic or polycyclic hydrocarbon groups, C1 to C15 heteroatom-containing heteromonocyclic or polycyclic groups, or C1 to C25 saturated or unsaturated chain-form or cyclic hydrocarbon groups. Here, $R^8$ and $R^9$ may be bonded to each other to form a ring.

The substituent in this case may be selected as appropriate from for example a hydrogen atom, a halogen atom, a nitro group, a cyano group, a hydroxy group, a sulfo group, a mercapto group, a carboxyl group, and a C1-10 alkyl group, C3-15 cycloalkyl group, C5 to 15 aryl group, C1-15 heterocyclyl group, C2-10 alkenyl group, C2-10 alkynyl group, C1-10 alkoxy group, C1-10 ester group, C1-10 fluoroalkyl group, C1-10 acyl group, C1-10 sulfonyl group, C1-10 amino group, C1-10 amide group, C1-10 sulfenyl group, or C1-10 silyl group in which one or more hydrogen atoms are optionally substituted.

Specific examples of $R^8$ and $R^9$ include an aromatic monocyclic or polycyclic group such as a phenyl group, 2-methylphenyl, 2-ethylphenyl, 2-isopropylphenyl, 2-tert-butylphenyl, 2-methoxyphenyl, 2-chlorophenyl, 2-vinylphenyl, 3-methylphenyl, 3-ethylphenyl, 3-isopropylphenyl, 3-methoxyphenyl, 3-chlorophenyl, 3-vinylphenyl, 4-methylphenyl, 4-ethylphenyl, 4-isopropylphenyl, 4-tert-butylphenyl, 4-vinylphenyl, cumenyl, mesityl, xylyl, 1-naphthyl, 2-naphthyl, anthryl, phenanthryl, or indenyl group, a heteromonocyclic or polycyclic group such as thienyl, furyl, pyranyl, xanthenyl, pyridyl, pyrrolyl, imidazolinyl, indolyl, carbazoyl, or Phenanthrolinyl, an alkyl group such as methyl, ethyl, propyl, butyl, pentyl, hexyl, or heptyl, a cycloalkyl group such as cyclopropyl, cyclobutyl, cyclopentyl, cyclohexyl, or 2-adamantyl, an unsaturated hydrocarbon group such as benzyl, vinyl, or aryl, and a ferrocenyl group.

When $R^8$ and $R^9$ are bonded to form a ring, examples include saturated and unsaturated alicyclic groups that give a cyclic alcohol such as cyclopentanol, cyclohexanol, cycloheptanol, cyclopentenol, cyclohexenol, or cycloheptenol, and saturated and unsaturated alicyclic groups having on each carbon an alkyl group, an aryl group, an unsaturated alkyl group, or a hetero element-containing chain-form or cyclic hydrocarbon group-containing substituent.

Examples of the formate include, but are not limited to, a metal formate such as sodium formate or potassium formate and a formate such as ammonium formate.

In the present specification, a dehydrogenation reaction means a reaction in which a hydrogen molecule is removed, and examples include an oxidative dehydrogenation reaction and a decomposition reaction. The dehydrogenation method of the present specification is carried out by a dehydrogenation reaction.

One aspect of the present invention relates to a method for producing from the alcohol the corresponding carbonyl compound by means of the dehydrogenation method of the present invention. For example, when the alcohol is a primary alcohol, an aldehyde is obtained as the corresponding carbonyl compound, as shown by for example the following reaction formula.

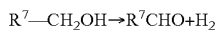 [Formula 2]

$R^7$ is as described above.

When it is a secondary alcohol, a ketone is obtained, as shown by for example the following reaction formula.

[Formula 3]

$R^8$ and $R^9$ are as described above.

One aspect of the present invention relates to a method for producing a carboxylic acid from a primary alcohol via an aldehyde using the dehydrogenation method of the present invention. It is thought that this conversion from an alcohol to a carboxylic acid progresses via three steps, that is, 1) formation of an aldehyde by dehydrogenation of the alcohol, 2) formation of a hemiacetal by hydration of the aldehyde, and 3) formation of a carboxylic acid by dehydrogenation of the hemiacetal. Therefore, when producing a carboxylic acid, it is preferable to use a solvent containing water in order to hydrate the aldehyde to form the hemiacetal. Specific examples of the production include, but are not limited to, production of acetic acid from ethanol.

One aspect of the present invention relates to a method for producing hydrogen from an alcohol, preferably a primary alcohol, using the dehydrogenation method of the present invention. The alcohol is not particularly limited, but is preferably a primary alcohol from the viewpoint of hydrogen generation efficiency, and is preferably produced by dehydrogenation of a solution in which it is mixed with water. For example, when the primary alcohol is methanol, 3 moles of molecular hydrogen are formed by dehydrogenation of a mixed solution of 1 mole of methanol:water=1:1, and formally all the hydrogen atoms in a methanol molecule and all of the hydrogen atoms in a water molecule are converted into hydrogen molecules, which is very efficient as a hydrogen production method.

In the production of hydrogen, a dehydrogenation reaction can progress at a pH of 1 to 14. From the viewpoint of hydrogen generation efficiency, the pH is preferably 5 to 14, and particularly preferably 10 to 14. Since carbon dioxide is generated accompanying progress of the reaction, and the reaction system gradually becomes acidic, efficient hydrogenation can be continued for a long period of time by setting the pH at the start of reaction at 13 or greater.

In accordance with the present invention, a carboxylic acid and hydrogen can be obtained from a primary alcohol at the same time. This enables a carboxylic acid, which is important in organic industrial chemistry, and hydrogen, which is useful as clean energy, to be obtained at the same time using as a starting material an alcohol obtained by fermentation from a biomass resource.

One aspect of the present invention relates to a method for producing hydrogen by a decomposition reaction of formic acid or a formate using the dehydrogenation method of the present invention. In accordance with the present invention, since it can be carried out at a reaction temperature of on the order of 60° C. to 90° C., it is excellent in terms of safety and economy and is very advantageous for industrial use.

In the dehydrogenation method of the present invention, the amount of catalyst used can be expressed as S/C (S is the number of moles of alcohol, formic acid, or formate, and C is the number of moles of catalyst), which is the molar ratio of alcohol, formic acid, or formate relative to ruthenium, rhodium, or iridium complex. In this case, the degree to which S/C can be increased greatly depends on the structure of the substrate, the type of catalyst, the concentration, the reaction temperature, the type of reaction solvent, etc, but in practice it is desirable to set S/C equal to on the order of 50 to 500000.

The dehydrogenation reaction of the present invention is carried out in the presence or absence of solvent. When a solvent is used, the reaction solvent may be selected as appropriate while taking into consideration the physical properties and the chemical properties of catalyst, substrate, and product. A protic solvent, an aprotic solvent, an ionic liquid, water, or a buffer may be used on their own or in a combination of a plurality thereof.

Specific examples of the solvent include, but are not limited to, pentane, hexane, heptane, benzene, toluene, xylene, tetrahydrofuran, diisopropyl ether, dichloromethane, dimethylformamide, t-butanol, and water.

The reaction temperature may preferably be on the order of −20° C. to 200° C., and more preferably 20° C. to 150° C., while taking into consideration solubility, reactivity, and economic efficiency of catalyst, substrate, and product.

With regard to the reaction time, although it varies depending on reaction conditions such as substrate concentration and reaction temperature, the reaction is completed in a few minutes to 100 hours.

Purification of a carbonyl compound prepared by the dehydrogenation reaction may be carried out by a known method such as acid-base extraction, column chromatography, distillation, or recrystallization, or by a combination thereof as appropriate.

In accordance with the dehydrogenation method of the present invention, a reaction is possible over a wide range of pH. In the dehydrogenation reaction of an alcohol, the pH may be 1 to 14, and preferably 4 to 10, and from a synthetic chemistry viewpoint the pH is preferably 6 to 8.

In the production of a carboxylic acid, the pH can change toward the acidic side accompanying formation of the carboxylic acid, but the reaction progresses in a pH region of 1 to 14. From a synthetic chemistry viewpoint it is preferable to start at a pH of 6 to 8, which is the neutral region, and from the viewpoint of efficiency of formation of a carboxylic acid it is preferable for the pH of the reaction system to be in the range of 1 to 10 throughout the reaction; it is particularly preferable for the pH to be in the range of 1 to 8.

One aspect of the present invention relates to an organometallic compound of Formula (1) below Formula (1)

[Chem. 7]

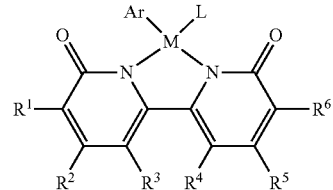

wherein

Ar is an optionally substituted benzene or an optionally substituted cyclopentadienyl group, M is ruthenium, rhodium, or iridium, $R^1$ to $R^6$ are mutually independently a hydrogen atom, a halogen atom, a nitro group, a cyano group, a hydroxy group, a sulfo group, a mercapto group, a carboxyl group, or a C1-10 alkyl group, C3-15 cycloalkyl group, C6-15 aryl group, C1-10 heterocyclyl group, C2-10 alkenyl group, C2-10 alkynyl group, C1-10 alkoxy group, C1-10 ester group, C1-10 fluoroalkyl group, C1-10 acyl group, C1-10 sulfonyl group, C1-10 amino group, C1-10 amide group, C1-10 sulfenyl group, or C1-10 silyl group in which one or more hydrogen atoms are optionally substituted, $R^3$ and $R^4$ may be bonded to each other to form —CH=CH—, the Hs in the —CH=CH— are optionally substituted mutually independently by a halogen atom, a nitro group, a cyano group, a hydroxy group, a sulfo group, a mercapto group, a carboxyl group, or a C1-10 alkyl group, C3-15 cycloalkyl group, C6-15 aryl group, C1-10 heterocyclyl group, C2-10 alkenyl group, C2-10 alkynyl group, C1-10 alkoxy group, C1-10 ester group, C1-10 fluoroalkyl group, C1-10 acyl group, C1-10 sulfonyl group, C1-10 amino group, C1-10 amide group, C1-10 sulfenyl group, or C1-10 silyl group in which one or more hydrogen atoms are optionally substituted, and L is an aquo ligand.

One aspect of the present invention relates to an organometallic compound of Formula (2) below

[Chem. 8]

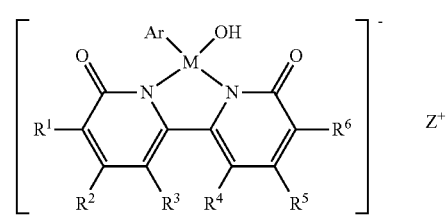

wherein

Ar is an optionally substituted benzene or an optionally substituted cyclopentadienyl group, M is ruthenium, rhodium, or iridium, $R^1$ to $R^6$ are mutually independently a hydrogen atom, a halogen atom, a nitro group, a cyano group, a hydroxy group, a sulfo group, a mercapto group, a carboxyl group, or a C1-10 alkyl group, C3-15 cycloalkyl group, C6-15 aryl group, C1-10 heterocyclyl group, C2-10 alkenyl group, C2-10 alkynyl group, C1-10 alkoxy group, C1-10 ester group, C1-10 fluoroalkyl group, C1-10 acyl group, C1-10 sulfonyl group, C1-10 amino group, C1-10 amide group, C1-10 sulfenyl group, or C1-10 silyl group in which one or more hydrogen atoms are optionally substituted, $R^3$ and $R^4$ may be bonded to each other to form —CH═CH—, the Hs in the —CH═CH— are optionally substituted mutually independently by a halogen atom, a nitro group, a cyano group, a hydroxy group, a sulfo group, a mercapto group, a carboxyl group, or a C1-10 alkyl group, C3-15 cycloalkyl group, C6-15 aryl group, C1-10 heterocyclyl group, C2-10 alkenyl group, C2-10 alkynyl group, C1-10 alkoxy group, C1-10 ester group, C1-10 fluoroalkyl group, C1-10 acyl group, C1-10 sulfonyl group, C1-10 amino group, C1-10 amide group, C1-10 sulfenyl group, or C1-10 silyl group in which one or more hydrogen atoms are optionally substituted, and Z is Na, Li, K, or Cs.

A compound of Formula (2) may be produced by a reaction between an alkaline compound and an organometallic compound of Formula (1) where L is an aquo ligand. Examples of the alkaline compound include, but are not limited to, sodium hydroxide, lithium hydroxide, potassium hydroxide, and cesium hydroxide. Therefore, a compound of Formula (2) may be prepared in the reaction system by adding an alkaline compound in a dehydrogenation reaction using as a catalyst an organometallic compound of Formula (1) where L is an aquo ligand.

A compound of Formula (2) may be used in the same way as for a compound of Formula (1) in the dehydrogenation method, the method for producing a carbonyl compound, the method for producing hydrogen, etc. described above for a compound of Formula (1). Therefore, the present invention relates to a dehydrogenation catalyst containing a compound of Formula (2).

The method for producing hydrogen according to the present invention involves producing hydrogen continuously from a mixture of an alcohol and water. From the viewpoint of efficiency in particular, it is preferable to use a compound of Formula (2).

As methods for continuously producing hydrogen there can be cited, for example, a consecutive addition method and a continuous addition method. The consecutive addition method involves adding to a mixture of an alcohol and water a compound of Formula (1) and/or Formula (2) and an alkaline compound, carrying out a reaction under reflux by heating to thus generate hydrogen, then adding amounts of alcohol and water corresponding to those consumed, and further adding an alkaline compound. It is preferable for the pH after each addition to be identical to the pH at the time of starting the reaction. In this way, by consecutively adding the amounts consumed, hydrogen can be produced continuously.

The continuous addition method involves adding a compound of Formula (1) and/or Formula (2) and an alkaline compound to a mixture of an alcohol and water, starting the reaction system under reflux by heating, and continuing to add a premixed mixture of alcohol, water, and alkaline compound using for example a syringe pump, a micro-feeder, etc. in a state in which reflux is continued. In this way, hydrogen gas can be produced at a substantially constant rate for a long period of time by continuously carrying out a reaction while replenishing the amounts, corresponding to the rate at which they are consumed, of the starting materials (alcohol and water) and sodium hydroxide that are consumed continuously at a constant rate.

In accordance with the method for producing hydrogen, in which hydrogen is produced continuously, according to the present invention, it is possible to achieve a catalytic turnover number of at least 2, at least 100, preferably at least 1000, and more preferably at least 3500, and it is possible to construct a new system having very high efficiency and high practicality.

Examples of a system for continuously producing hydrogen include, but are not limited to, a system containing a reaction vessel, a supply section, and a recovery section. The reaction vessel is not particularly limited as long as it can subject a starting material to a dehydrogenation reaction in the presence of a catalyst, but is preferably one in which the reaction can be made continuous, and is typically equipped with devices that can carry out heating and refluxing. The supply section typically contains storage vessels for storing starting materials and alkaline compound for replenishment addition, and supply means such as a syringe pump or a micro-feeder. The recovery section is not particularly limited as long as it recovers the hydrogen generated, and examples include a gas burette, a gas bag, and a gas tank.

One aspect of the present invention relates not only to the dehydrogenation reaction but also to hydrogenation and interconversion by reversible dehydrogenation-hydrogenation. For example, in a catalytic reaction of reaction formula (II)

[Formula 4]

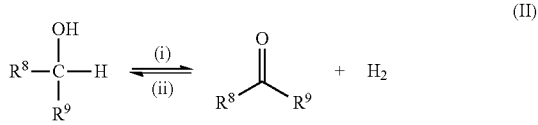

(II)

wherein $R^8$ and $R^9$ are as described above, (i) is a dehydrogenation reaction and (ii) is hydrogenation, the catalyst of the present invention can repeatedly carry out quantitative interconversion, that is, catalytic reactions in both directions (i) and (ii), accompanied by release and absorption of hydrogen.

By reversibly and continuously carrying out a dehydrogenation reaction and hydrogenation using the same catalyst, it can be expected that the system will be developed as a hydrogen storage system.

EXAMPLES

The present invention is explained below in further detail by reference to Examples, but the present invention should not be construed as being limited by these Examples.

The reactions described in the Examples below were carried out under an atmosphere of an inert gas such as argon gas or nitrogen gas. As the alcohols used, commercial reagents were used as they were. Identification of complexes and reaction products was carried out using a nuclear magnetic resonance (NMR) machine with tetramethylsilane (TMS) as an internal reference substance, the signal thereof being δ=0 (δ: chemical shift). The conversion and yield of carbonyl compound and hydrogen were determined by gas chromatography (GC). For NMR, JOEL ECX-500 and JOEL ECS-400 machines (JEOL) were used, and for GC a GL-Sciences GC353B machine (G L Sciences Inc.) was used.

Synthesis of Novel Neutral Iridium Complex Catalyst

Production Example 1

Neutral iridium complex 1 was produced by the method shown in either production example 1-a or 1-b.

Production Example 1-a

As shown in synthetic scheme 1-a, a dicationic Cp* iridium-aquo complex (407.8 mg, 0.60 mmol) was reacted with 6,6'-dihydroxy-2,2'-bipyridine ligand (113.8 mg, 0.60 mmol) in aqueous solvent (12 mL) to thus give complex A (yield 93%). Subsequently, complex A (915.0 mg, 1.1 mmol) was reacted with sodium t-butoxide (211.4 mg, 2.2 mmol) in aqueous solvent (30 mL) to give neutral iridium complex 1 (yield 84%).

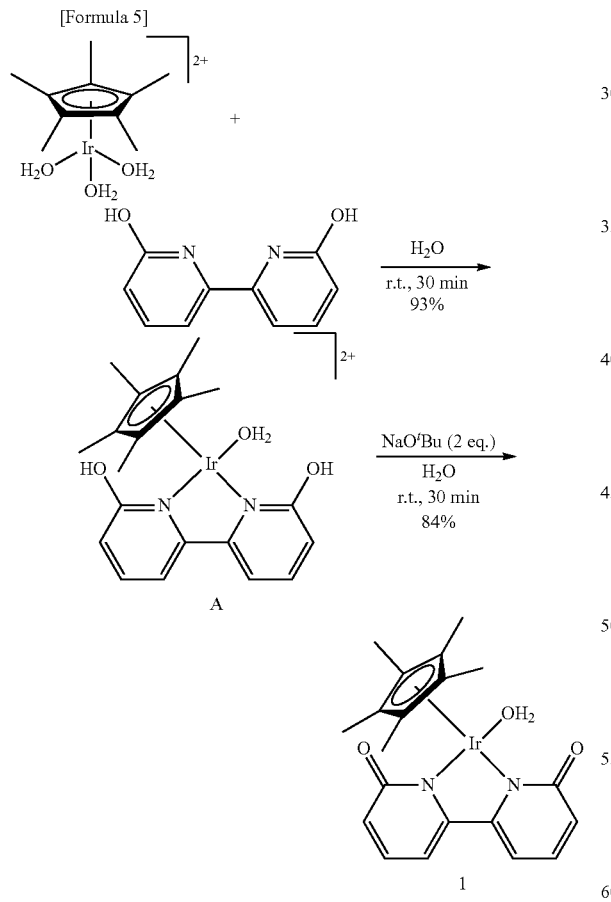

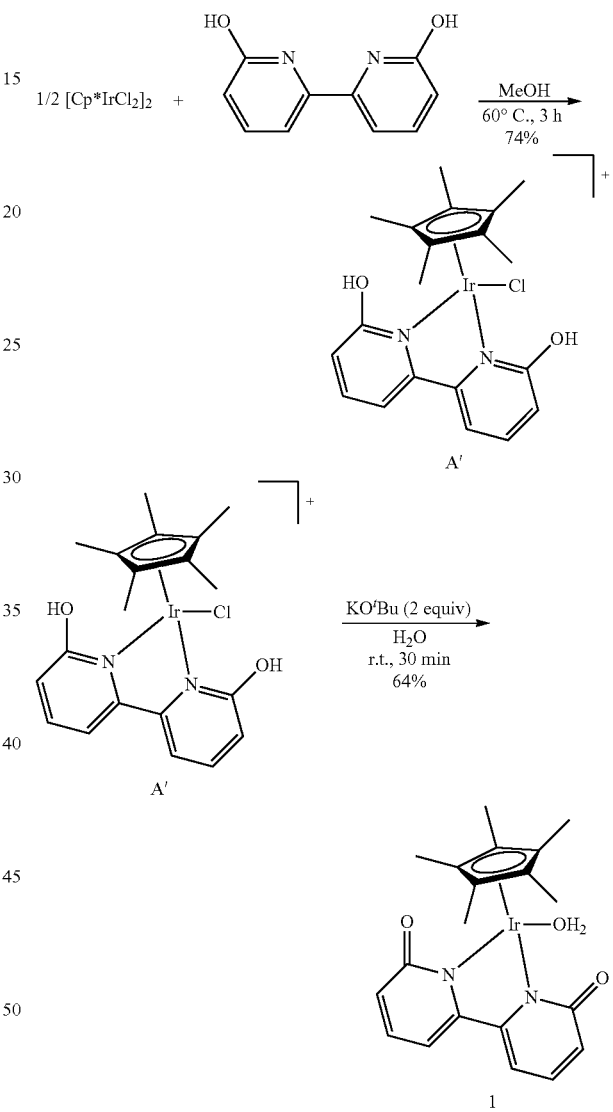

Production Example 1-b

As shown in scheme 1-b, [Cp*IrCl$_2$]$_2$ (458.4 mg, 0.570 mmol) was reacted with 6,6'-dihydroxy-2,2'-bipyridine ligand (250.0 mg, 1.33 mmol) in methanol solvent (8 mL), a reaction was carried out at 60° C. for 3 hours, and filtration using a glass filter was then carried out to thus give cationic complex A' (yield 74%). Subsequently, cationic complex A' (100.0 mg, 0.170 mmol) was reacted with potassium t-butoxide (38.3 mg, 0.340 mmol) in water (5 mL) at room temperature for 30 minutes while stirring, and a solid thus precipitated was filtered to thus give complex 1 (yield 64%).

$^1$H NMR (400 MHz, CD$_3$OD) δ 7.43 (t, J=8 Hz, 2H), 6.92 (d, J=8 Hz, 2H), 6.43 (d, J=8 Hz, 2H), 1.59 (s, 15H). $^{13}$C{$^1$H} NMR (125.8 MHz, CD$_3$OD) δ 170.9, 157.3, 139.9, 118.1, 106.9, 88.0, 9.83. Anal. Calcd for C$_{20}$H$_{23}$O$_3$N$_2$Ir: C, 45.18; H, 4.36; N, 5.27. Found: C, 45.47; H, 4.01; N, 5.62.

Production Example 2

Synthesis of Neutral Iridium Complex 2

As shown in scheme 2, [Cp*IrCl$_2$]$_2$ (240.0 mg, 0.301 mmol) was reacted with 2,9-dihydroxy-1,10-phenanthroline ligand (150.1 mg, 0.707 mmol) in methanol solvent (5.4 mL), a reaction was carried out at 60° C. for 4 hours, and filtration using a glass filter was then carried out to thus give cationic complex T (yield 60%). Subsequently, cationic complex T (150 mg, 0.229 mmol) was reacted with potassium t-butoxide (51.4 mg, 0.421 mmol) in water (6.8 mL) at room temperature for 30 minutes while stirring, and the solvent was removed by distillation under vacuum. The residue was extracted by adding toluene (15 mL), the solvent was removed by distillation, and recrystallization was then carried out using ethanol (2 mL) and water (18 mL) to thus give complex 2 (yield 73%).

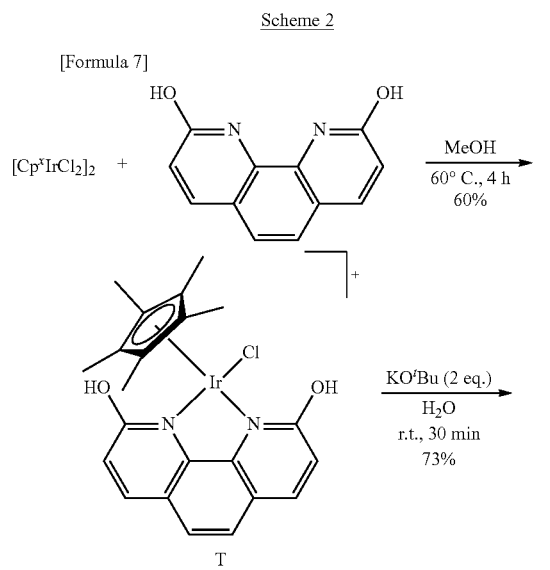

$^1$H NMR (400 MHz, CDCl$_3$) δ 7.78 (d, J=9 Hz, 2H), 7.16 (s, 2H), 6.81 (d, J=9 Hz, 2H), 1.86 (s, 15H). $^{13}$C{$^1$H} NMR (125.8 MHz, CDCl$_3$) δ 168.7, 146.1, 139.1, 123.5, 119.2, 118.8, 91.7, 10.8.

Production Example 3

Synthesis of Neutral Iridium Complex B

Cationic complex A' (150.6 mg, 0.240 mmol) was reacted with potassium t-butoxide (80.5 mg, 0.718 mmol) and pyridine (101.1 mg, 1.278 mmol) in dichloromethane (10 mL) at room temperature while stirring overnight, and the solvent was removed by distillation under vacuum. The residue was extracted by adding toluene (15 mL), and the solvent was then removed by distillation to thus give complex B (yield 75%).

$^1$H NMR (500 MHz, CD$_2$Cl$_2$) δ 9.87 (d, J=8 Hz, 2H), 7.58 (t, J=8 Hz, 1H), 7.16 (d, J=8 Hz, 2H), 6.22 (d, J=8 Hz, 2H) δ 1.50 (s, 15H). $^{13}$C{$^1$H} NMR (125.8 MHz, CD$_2$Cl$_2$) δ 168.8, 158.4, 157.4, 136.9, 136.7, 125.7, 117.6, 103.4, 88.2, 9.4.

Production Example 4

Synthesis of Neutral Iridium Complex C

Cationic complex A' (150.6 mg, 0.240 mmol) was reacted with potassium t-butoxide (80.5 mg, 0.718 mmol) and aniline (35.7 mg, 0.360 mmol) in dichloromethane (10 mL) at room temperature while stirring overnight, and the solvent was removed by distillation under vacuum. The residue was extracted by adding toluene (15 mL), and the solvent was then removed by distillation to thus give complex C (yield 70%).

$^1$H NMR (500 MHz, CD$_2$Cl$_2$) δ 7.49 (bs, 1H), 7.27 (bs, 2H), 7.23 (t, J=8 Hz, 2H), 7.06 (bs, 1H), 6.52 (d, J=7 Hz, 2H), 6.22 (d, J=8 Hz, 2H), 5.79 (bs, 1H), 1.28 (s, 15H). $^{13}$C{$^1$H} NMR (125.8 MHz, CD$_2$Cl$_2$) δ 169.1, 156.1, 141.5, 137.5, 128.6, 125.2, 122.5, 117.0, 103.4, 86.6, 8.4.

Production Example 5

Synthesis of Neutral Iridium Complex D

Cationic complex A' (150.6 mg, 0.240 mmol) was reacted with potassium t-butoxide (80.5 mg, 0.718 mmol) and dimethylsulfoxide (18.3 mg, 0.234 mmol) in dichloromethane (10 mL) at room temperature while stirring overnight, and the solvent was removed by distillation under vacuum. The residue was extracted by adding toluene (15 mL), and the solvent was then removed by distillation to thus give complex D (yield 61%).

$^1$H NMR (500 MHz, CD$_2$Cl$_2$) δ 7.15 (t, J=8 Hz, 2H), 6.46 (d, J=8 Hz, 2H), 6.13 (d, J=8 Hz, 2H), 2.89 (bs, 6H), 1.56 (s, 15H). $^{13}$C{$^1$H} NMR (100.5 MHz, CD$_2$Cl$_2$) δ 168.2, 156.6, 137.2, 117.2, 103.9, 95.1, 46.1, 9.0.

Production Example 6

Synthesis of Neutral Iridium Complex E

Cationic complex T (150.6 mg, 0.230 mmol) was reacted with potassium t-butoxide (79.2 mg, 0.706 mmol) and pyridine (90.5 mg, 1.144 mmol) in dichloromethane (10 mL) at room temperature while stirring overnight, and the solvent was removed by distillation under vacuum. The residue was extracted by adding toluene (15 mL), and the solvent was then removed by distillation to thus give complex E (yield 82%).

$^1$H NMR (500 MHz, CDCl$_3$) δ 9.65 (d, J=5 Hz, 1H), 7.56 (d, J=8 Hz, 2H), 7.53 (t, J=8 Hz, 2H), 7.19 (t, J=7 Hz, 2H), 6.68 (d, J=8 Hz, 2H), 1.59 (s, 15H). $^{13}$C{$^1$H} NMR (125.8 MHz, CD$_2$Cl$_2$) δ 168.2, 158.2, 147.4, 136.9, 136.8, 125.9, 122.6, 120.8, 118.7, 88.2, 10.0.

Dehydrogenation reactions using the complexes thus synthesized as catalysts are now illustrated. The structural formulae of the complexes used in the Examples are shown below.

Complexes Used in Examples

[Chem. 9]

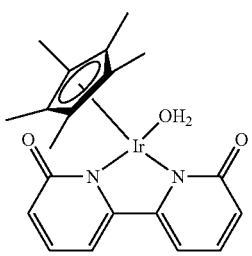

1

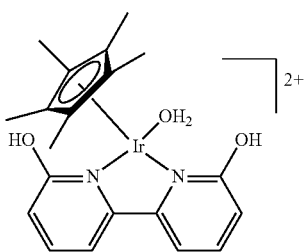

2

[Chem. 10]

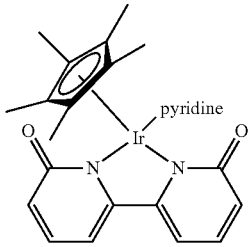

B

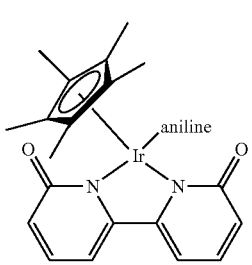

C

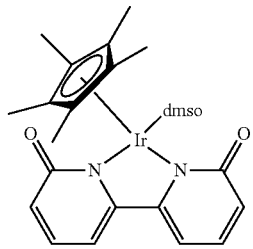

D

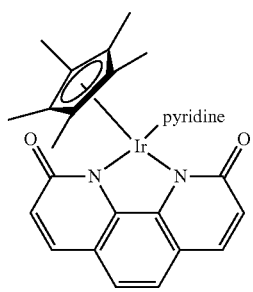

E

Example 1

Synthesis of Acetophenone by Dehydrogenation Reaction of Racemic 1-Phenylethanol Under an inert gas atmosphere a 50 mL two-necked recovery flask was charged with 3 mL of anhydrous pentane, 122.2 mg (1.0 mmol) of racemic 1-phenylethanol, and 2.7 mg (0.005 mmol, 0.5 mol %) of complex 1, and stirring was carried out under reflux conditions for 5 hours. 10 mL of toluene was added thereto and the mixture was made uniform, and when the reaction solution was then analyzed by GC it was confirmed that the corresponding acetophenone was formed with a conversion factor of 100% and a yield of 100% as shown in Table 1.

Example 2

Synthesis of Acetophenone by Dehydrogenation Reaction of Racemic 1-Phenylethanol A reaction was carried out under the same conditions as those of Example 1 except that 2.8 mg (0.005 mmol, 0.5 mol %) of complex 2 was used as a catalyst. From the result of analysis by GC, it was confirmed that acetophenone was formed with a conversion factor of 37% and a yield of 36% as shown in Table 1.

Examples 3 to 6

Synthesis of Acetophenone by Dehydrogenation Reaction of Racemic 1-Phenylethanol Reactions were carried out under the same conditions as those of Example 1 except that the various types of complex catalyst B to E (0.005 mmol) shown in Table 1 were used as catalyst. The results of analysis by GC are summarized in Table 1. It was confirmed that acetophenone was formed.

TABLE 1

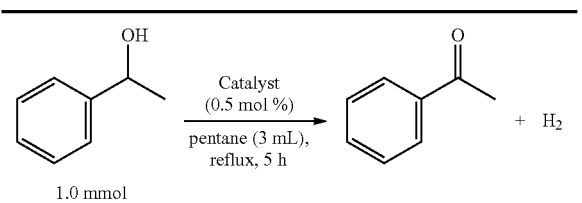

| Example | Catalyst | Conversion Factor (%) | Yield (%) |
|---|---|---|---|
| Example 1 | 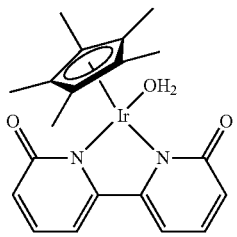 1 | 100 | 100 |
| Example 2 | 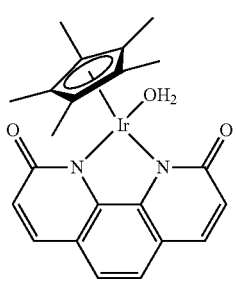 2 | 37 | 36 |
| Example 3 | 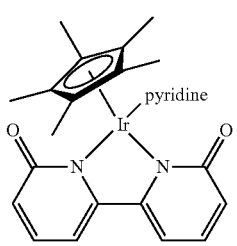 B | 8 | 7 |
| Example 4 | 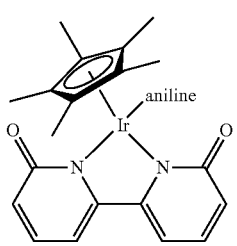 C | 11 | 10 |

TABLE 1-continued

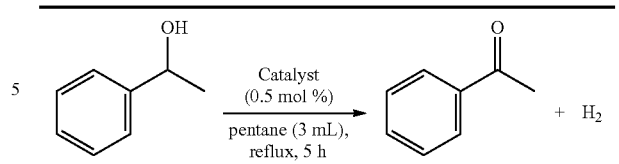

| Example | Catalyst | Conversion Factor (%) | Yield (%) |
|---|---|---|---|
| Example 5 | 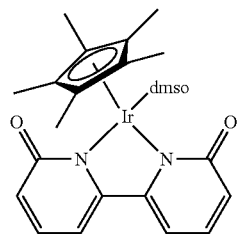 D | 17 | 16 |
| Example 6 | 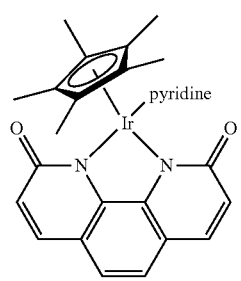 E | 9 | 8 |

Example 7

Synthesis of Acetophenone by Dehydrogenative Oxidation Reaction of Racemic 1-Phenylethanol Under an inert gas atmosphere a 50 mL two-necked recovery flask was charged with 3 mL of anhydrous pentane, 122.2 mg (1.0 mmol) of racemic 1-phenylethanol, and 2.7 mg (0.005 mmol, 0.5 mol %) of complex 1, and stirring was carried out under reflux conditions for 5 hours. 10 mL of toluene was added thereto and the mixture was made uniform, and when the reaction solution was then analyzed by GC it was confirmed that the corresponding acetophenone was formed with a conversion factor of 100% and a yield of 100% as shown in Table 2.

Comparative Example 1

Synthesis of Acetophenone by Dehydrogenative Oxidation Reaction of Racemic 1-Phenylethanol A reaction was carried out under the same conditions as those of Example 7 except that complex A (0.005 mmol) was used as a catalyst. From the result of analysis by GC, it was found that acetophenone was prepared with a conversion factor of 19% and a yield of 18% as shown in Table 2. Compared with Example 7, the yield was clearly low, showing the effectiveness of the present invention.

Comparative Example 2

Synthesis of Acetophenone by Dehydrogenative Oxidation Reaction of Racemic 1-Phenylethanol A reaction was carried out under the same conditions as those of Example 7 except that complex A (0.005 mmol) was used as a catalyst and water was used as a reaction solvent. From the result of analysis by GC, it was found that acetophenone was prepared with a conversion factor of 6% and a yield of 4% as shown in Table 2. Compared with Example 7, the yield was clearly low, showing the effectiveness of the present invention.

Comparative Example 3

Synthesis of Acetophenone by Dehydrogenative Oxidation Reaction of Racemic 1-Phenylethanol A reaction was carried out under the same conditions as those of Example 7 except that complex A (0.005 mmol) was used as a catalyst, water was used as a reaction solvent, and the reaction was carried out at 80° C. From the result of analysis by GC, it was found that acetophenone was prepared with a conversion factor of 12% and a yield of 11% as shown in Table 2. Compared with Example 7, the yield was clearly low, showing the effectiveness of the present invention.

TABLE 2

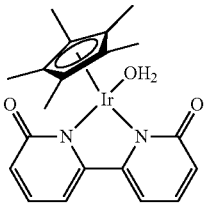

| Example and Comparative Example | Catalyst | Solvent | Temp. (° C.) | Conv. factor (%) | Yield (%) |
|---|---|---|---|---|---|
| Ex. 7 | 1 | pentane | 36 (reflux) | 100 | 100 |
| Comp. Ex. 1 | A | pentane | 36 (reflux) | 19 | 18 |
| Comp. Ex. 2 | A | $H_2O$ | 36 | 6 | 4 |
| Comp. Ex. 3 | A | $H_2O$ | 80 | 12 | 11 |

Examples 8 to 14

Synthesis of Ketone by Dehydrogenative Oxidation Reaction of Secondary Alcohol Dehydrogenative oxidation reactions of various secondary alcohols were carried out using complex 1 as a catalyst under the reaction conditions shown in Table 3. After the reactions were completed, when the reaction solutions were analyzed by GC it was confirmed that ketones were formed with a high conversion factor and a high yield in all cases.

TABLE 3

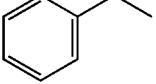

| Example | Alcohol | Catalyst (mol %) | Solvent | Time (h) | Conv. factor (%) | Yield (%) |
|---|---|---|---|---|---|---|
| Example 8 | (1-phenylethanol) | 0.5 | pentane | 5 | 100 | 100 |

TABLE 3-continued

Catalyst 1, Solvent (3 mL), reflux
R⁸R⁹CHOH (1.0 mmol) → R⁸R⁹C=O + H₂

| Example | Alcohol | Catalyst (mol %) | Solvent | Time (h) | Conv. factor (%) | Yield (%) |
|---|---|---|---|---|---|---|
| Example 9 | 4-MeO-C₆H₄-CH(OH)-CH₃ | 0.5 | pentane | 5 | 100 | 100 |
| Example 10 | 4-Br-C₆H₄-CH(OH)-CH₃ | 1.0 | pentane | 5 | 90 | 90 |
| Example 11 | 4-O₂N-C₆H₄-CH(OH)-CH₃ | 2.0 | pentane | 20 | 86 | 85 |
| Example 12 | cyclopentanol | 1.0 | hexane | 20 | 100 | 100 |
| Example 13 | cyclohexanol | 1.0 | hexane | 20 | 95 | 94 |
| Example 14 | 2-octanol | 2.0 | hexane | 20 | 89 | 88 |

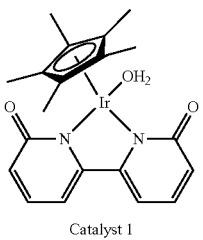

Catalyst 1

Example 15

Synthesis of Acetophenone by Dehydrogenative Oxidation Reaction of Racemic 1-Phenylethanol A 1000 mL recovery flask was charged with 500 mL of anhydrous p-xylene, 61.06 g (500 mmol) of racemic 1-phenylethanol, and 0.53 mg (0.001 mmol, 0.0002 mol %) of complex 1, and stirring was carried out under reflux conditions for 48 hours. Dichloromethane was added thereto and the mixture was made uniform, and when the reaction solution was then analyzed by GC it was confirmed that the corresponding acetophenone was formed at a yield of 55%. Since a high catalytic turnover number (TON=275,000) was shown in this reaction, the effectiveness of the present invention was shown.

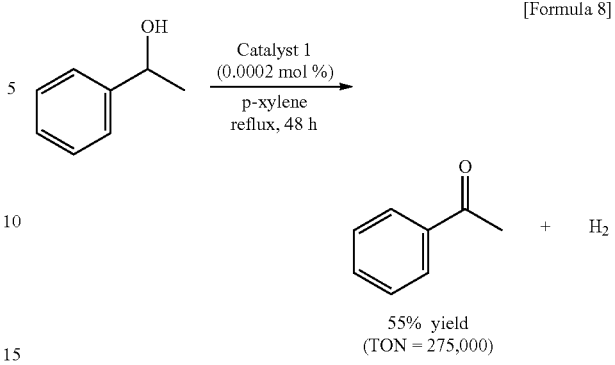

[Formula 8]

55% yield (TON = 275,000)

Example 16

Synthesis of Estrone by Dehydrogenative Oxidation Reaction of β-Estradiol

A 50 mL one-neck recovery flask was charged with 3 mL of tert-butyl alcohol, 272.4 mg (1.0 mmol) of β-estradiol, and 2.7 mg (0.005 mmol, 0.5 mol %) of complex 1, and stirring was carried out under reflux conditions for 20 hours. The solvent of the reaction solution was removed by distillation, and when analysis by NMR was carried out it was confirmed that the corresponding estrone was formed at a yield of 100%.

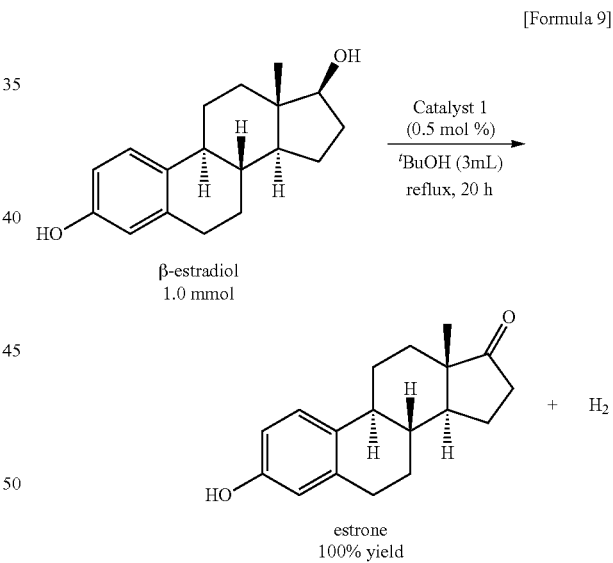

[Formula 9]

β-estradiol 1.0 mmol estrone 100% yield

Example 17

Synthesis of Benzaldehyde by Dehydrogenative Oxidation Reaction of Benzyl Alcohol A 50 mL recovery flask was charged with 10 mL of tert-butyl alcohol, 54.0 mg (0.5 mmol) of benzyl alcohol, and 4.0 mg (0.0075 mmol, 1.5 mol %) of complex 1, and stirring was carried out under reflux conditions for 20 hours. 10 mL of dichloromethane was added thereto and the mixture was made uniform, and when the reaction solution was then analyzed by GC it was confirmed that the corresponding benzaldehyde was formed with a conversion factor of 92% and a yield of 92% as shown in Table 4.

Examples 18 to 20

Synthesis of Aldehyde by Dehydrogenative Oxidation Reaction of Primary Alcohol

Reactions were carried out under the same conditions as those of Example 17 except that the various types of primary alcohols (0.5 mmol) shown in Table 4 were used as a substrate. The results of analysis by GC are summarized in Table 4.

Example 21

Synthesis of 4-(Trifluoromethyl)Benzaldehyde by Dehydrogenative Oxidation Reaction of 4-(Trifluoromethyl)Benzyl Alcohol A 50 mL recovery flask was charged with 10 mL of anhydrous heptane, 88.5 mg (0.5 mmol) of 4-(trifluoromethyl) benzyl alcohol, and 7.9 mg (0.015 mmol, 3.0 mol %) of complex 1, and stirring was carried out under reflux conditions for 20 hours. 10 mL of dichloromethane was added thereto and the mixture was made uniform, and when the reaction solution was then analyzed by GC it was confirmed that the corresponding 4-(trifluoromethyl)benzaldehyde was formed with a conversion factor of 89% and a yield of 88% as shown in Table 4.

Example 22

Synthesis of Cyclohexanecarboxyaldehyde by Dehydrogenative Oxidation Reaction of Cyclohexanemethanol A 50 mL recovery flask was charged with 10 mL of anhydrous toluene, 56.2 mg (0.5 mmol) of cyclohexanemethanol, and 6.5 mg (0.012 mmol, 2.5 mol %) of complex 1, and stirring was carried out under reflux conditions for 20 hours. 10 mL of toluene was added thereto and the mixture was made uniform, and when the reaction solution was then analyzed by GC it was confirmed that the corresponding cyclohexanecarboxyaldehyde was formed with a conversion factor of 82% and a yield of 81% as shown in Table 4.

Example 23

Synthesis of n-Octanal by Dehydrogenative Oxidation Reaction of 1-Octanol

A 50 mL recovery flask was charged with 10 mL of anhydrous toluene, 65.2 mg (0.5 mmol) of 1-octanol, and 13.2 mg (0.025 mmol, 5.0 mol %) of complex 1, and stirring was carried out under reflux conditions for 20 hours. 10 mL of toluene was added thereto and the mixture was made uniform, and when the reaction solution was then analyzed by GC it was confirmed that the corresponding n-octanal was formed with a conversion factor of 89% and a yield of 87% as shown in Table 4.

TABLE 4

$$R^7\text{-CH}_2\text{OH} \xrightarrow[\text{Solvent, reflux, 20 h}]{\text{Catalyst 1}} R^7\text{CHO} + H_2$$

0.5 mmol

| Example | Alcohol | Catalyst (mol %) | Solvent | Conv. factor (%) | Yield (%) |
|---|---|---|---|---|---|
| Example 17 | benzyl alcohol | 1.5 | tBuOH | 92 | 92 |
| Example 18 | 4-methoxybenzyl alcohol | 1.5 | tBuOH | 98 | 97 |
| Example 19 | 4-chlorobenzyl alcohol | 1.5 | tBuOH | 90 | 90 |
| Example 20 | 4-bromobenzyl alcohol | 1.5 | tBuOH | 89 | 87 |
| Example 21 | 4-(trifluoromethyl)benzyl alcohol | 3.0 | heptane | 89 | 88 |
| Example 22 | cyclohexanemethanol | 2.5 | toluene | 82 | 81 |
| Example 23 | 1-octanol | 5.0 | toluene | 89 | 87 |

Catalyst 1

Example 24

Synthesis of Benzaldehyde by Dehydrogenative Oxidation Reaction of Benzyl Alcohol A 500 mL recovery flask was charged with 270 mL of anhydrous toluene, 8.648 g (80 mmol) of benzyl alcohol, and 0.85 mg (0.0016 mmol, 0.002 mol %) of complex 1, and stirring was carried out under reflux conditions for 48 hours. Toluene was added thereto and the mixture was made uniform, and when the reaction solution was then analyzed by GC it was confirmed that the corresponding benzaldehyde was formed at a yield of 95%. Since in this reaction a high catalytic turnover number (TON=47,500) was shown, the effectiveness of the present invention was exhibited.

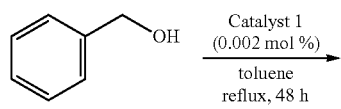

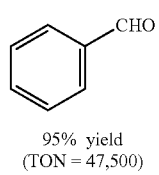 + H₂

95% yield
(TON = 47,500)

Example 25

Synthesis of Acetophenone by Dehydrogenative Oxidation Reaction of Racemic 1-Phenylethanol (Under Solvent-Free Conditions)

A 50 mL two-necked recovery flask was charged with 610.4 mg (5.0 mmol) of racemic 1-phenylethanol and 79.7 mg (0.15 mmol, 3.0 mol %) of complex 1 and stirring was carried out at 60° C. for 20 hours. 100 mL of dichloromethane was added thereto and the mixture was made uniform, and when the reaction solution was then analyzed by GC it was confirmed that the corresponding acetophenone was formed with a conversion factor of 95% and a yield of 93% as shown in Table 5.

Examples 26 to 28

Synthesis of Aldehyde by Dehydrogenative Oxidation Reaction of Alcohol (Under Solvent-Free Conditions)

Reactions were carried out under the same conditions as those of Example 25 except that the various types of alcohols (5.0 mmol) shown in Table 5 were used as a substrate and the reaction temperature was 90° C. The results of analysis by GC are summarized in Table 5.

Comparative Example 4

Synthesis of Acetophenone by Dehydrogenative Oxidation Reaction of Racemic 1-Phenylethanol (Under Solvent-Free Conditions)

A reaction was carried out under the same conditions as those of Example 25 except that complex A (0.15 mmol) was used as a catalyst. From the result of analysis by GC, as shown in Table 5 the conversion factor was 93%, but the yield of acetophenone was 5%. Since, compared with example 25, the yield was clearly low, the effectiveness of the present invention was exhibited.

TABLE 5

| Example and Comparative Example | Alcohol | Catalyst | Temp. (° C.) | Conv. factor (%) | Yield (%) |
|---|---|---|---|---|---|
| Example 25 | 1-phenylethanol | 1 | 60 | 95 | 93 |
| Example 26 | cyclopentanol | 1 | 90 | 91 | 89 |
| Example 27 | 2-octanol | 1 | 90 | 83 | 81 |
| Example 28 | benzyl alcohol | 1 | 90 | 41 | 35 |
| Comp. Ex. 4 | 1-phenylethanol | A | 60 | 93 | 5 |

Example 29

Synthesis of Acetic Acid Via Dehydrogenative Oxidation Reaction of Ethanol

A 10 mL test tube was charged with 460.7 mg (10 mmol) of ethanol, 360.4 mg (20 mmol) of water, and 159.7 mg (0.3 mmol, 3.0 mol %) of complex 1, and stirring was carried out under reflux conditions for 20 hours. When the reaction solution was analyzed by NMR, it was confirmed that acetic acid was formed at a yield of 75%. When the gas that was generated was analyzed, it was confirmed that hydrogen was formed at a yield of 84%. Since ethanol, which is obtained by fermentation from a biomass resource, was used as the starting material, and acetic acid, which is important in organic industrial chemistry, and hydrogen, which is useful as clean energy, could be obtained at the same time, the effectiveness of the present invention was exhibited.

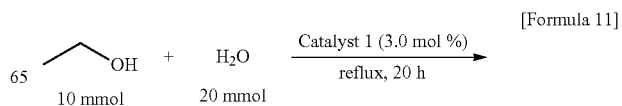

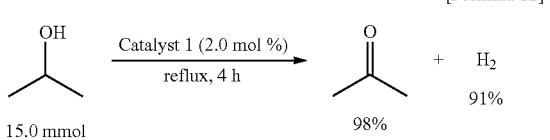

Example 30

Production of Hydrogen by Dehydrogenative Oxidation Reaction of 2-Propanol

A 10 mL test tube was charged with 901.6 mg (15 mmol) of 2-propanol and 159.5 mg (0.3 mmol, 2.0 mol %) of complex 1, and stirring was carried out under reflux conditions for 4 hours. When the reaction solution was analyzed by GC, it was confirmed that acetone was formed at a yield of 98%. When the gas that was generated was analyzed, it was confirmed that hydrogen was formed at a yield of 91%.

[Formula 12]

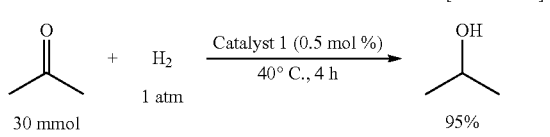

Example 31

Hydrogenation of Acetone

Under an inert gas atmosphere, a 30 mL two-necked recovery flask was charged with 79.6 mg (0.15 mmol, 0.5 mol %) of complex 1, flushed with hydrogen, then charged with 1.7418 g (30.0 mmol) of acetone, equipped with a balloon filled with hydrogen, and stirred at 40° C. for 4 hours. When the reaction solution was analyzed by GC, it was confirmed that 2-propanol was formed at a yield of 95%.

[Formula 13]

Example 32

Production of Hydrogen by Dehydrogenative Oxidation Reaction of Methanol

A 10 mL test tube was charged with 320.4 mg (10 mmol) of methanol, 180.2 mg (10 mmol) of water, and 159.5 mg (0.3 mmol, 3.0 mol %) of complex 1, an aqueous solution of sodium hydroxide was added until the pH, by pH meter, exceeded 13, and stirring was carried out under reflux conditions for 20 hours. When the gas that was generated was analyzed, it was confirmed that hydrogen was formed at a yield of 99%.

[Formula 14]

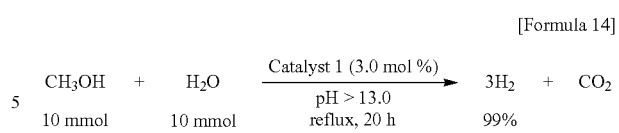

Example 33

Production of Hydrogen by Dehydrogenative Oxidation Reaction of Formic Acid A 10 mL test tube was charged with 460.6 mg (10 mmol) of formic acid and 2.6 mg (0.005 mmol, 0.05 mol %) of complex 1, and stirring was carried out at 60° C. for 21 minutes. When the gas that was generated was analyzed, it was confirmed that hydrogen was formed at a yield of 94%. Since formic acid could be decomposed with a small amount of catalyst in a short period of time to thus produce hydrogen, the effectiveness of the present invention was exhibited.

[Formula 15]

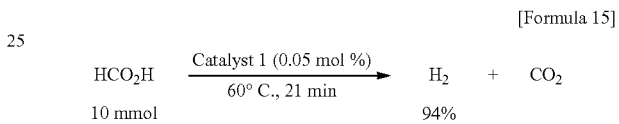

Production Example 7

Synthesis of Anionic Iridium Complex Having Functional Bipyridonate Ligand

A flask was charged with neutral iridium complex 1 (1.0630 g, 2.0 mmol), a 1.0 M aqueous solution of sodium hydroxide (3.0 mL, 3.0 mmol) was added thereto, a reaction was carried out at room temperature, and a dark green uniform solution was obtained. The solution was subsequently transferred to a micro tube and crystallized by allowing it to stand while open to the air, thus giving the novel anionic complex 3 having sodium ion as the counterion at a yield of 72% (796.5 mg, 1.4 mmol).

$^1$H NMR (500 MHz, D$_2$O) δ 7.46 (t, J=8.0 Hz, 2H), 7.03 (d, J=6.5 Hz, 2H), 6.42 (d, J=7.5 Hz, 2H), 1.49 (s, 15H). $^{13}$C{$^1$H}NMR (125.8 MHz, D$_2$O) δ 170.6, 156.9, 139.3, 116.8, 107.4, 85.6, 9.39. Anal. Calcd for C$_{20}$H$_{22}$O$_3$N$_2$NaIr.H$_2$O: C, 42.02; H, 4.23; N, 4.90. Found: C, 42.07; H, 4.64; N, 4.93.

[Formula 16]

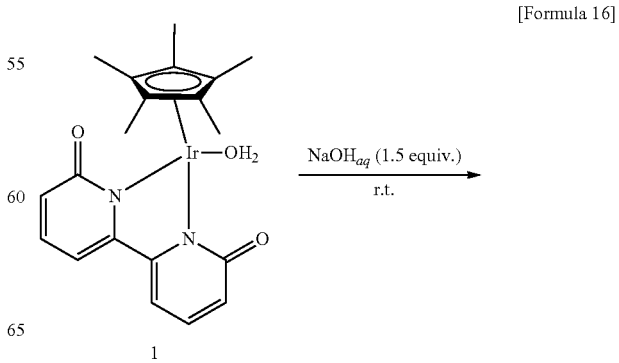

-continued

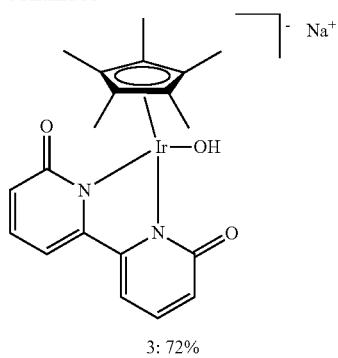

3: 72%

Catalytic reactions using complex 3, dicationic complex A, and neutral iridium complex 1 as catalysts were examined, as follows.

[Chem. 11]

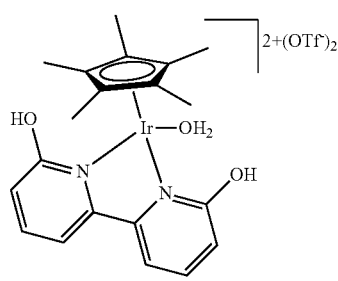

A

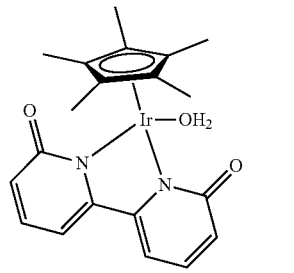

1

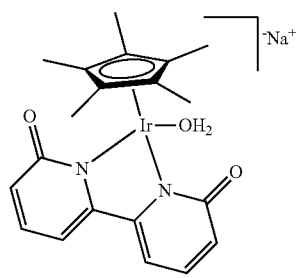

3

Example 34

Reaction Involving Generation of Hydrogen from Mixture of Methanol and Water

Dehydrogenation reactions from a mixture of methanol and water were carried out using complexes A, 1, and 3 described above as catalysts. The reactions were carried out using methanol and water as starting materials in the presence of catalyst while heating and refluxing, and the gas that was generated was collected in a gas burette and quantitatively measured. Of the volume of gas, 75% was considered to be hydrogen, and the volume and yield of hydrogen were calculated and are listed in the table. First, equal parts of methanol (20 mmol) and water (20 mmol) were used as starting materials, they were heated and refluxed in the presence of catalyst A, 1, and 3 (0.5 mol %) for 20 hours, and the activities of the catalysts were compared (entries 1-3). The reaction hardly progressed when catalyst A, which is dicationic, or catalyst 1, which is neutral, was used, and it was observed that only a very small amount of hydrogen was generated (entries 1 and 2), but the reaction progressed with the use of catalyst 3, which is anionic, and 120 mL (yield 8%) of hydrogen could be obtained (entry 3). Second, the number of equivalents of water relative to methanol was changed (entries 3-5), and when four equivalents of water were used a maximum amount of hydrogen was generated (150 mL, yield 10%, entry 4). Subsequently, since in this catalyst system carbon dioxide is generated accompanying the progress of the reaction, the system gradually becomes acidic, it can be expected that the catalyst molecule will be converted from anionic complex 3 to neutral complex 1 and further to dicationic complex A, and in order to prevent this the addition of a base (sodium hydroxide) as an additive was investigated (entries 6-9). This greatly improved the yield of hydrogen; the optimum conditions were obtained when 0.5 mol % of sodium hydroxide was added, and 1223 mL (yield 84%) of hydrogen was obtained (entry 7).

TABLE 6

$$CH_3OH + H_2O \xrightarrow[\text{Reflux, 20 hr}]{\text{Catalyst (0.5 mol \%)}} 3 H_2 + CO_2$$

20 mmol

| entry | Catalyst | H$_2$O (equiv.) | Additive (mol %) | Volume of hydrogen generated (mL) | Yield of hydrogen (%) |
|---|---|---|---|---|---|
| 1 | A | 1.0 | none | 4 | >1 |
| 2 | 1 | 1.0 | none | 11 | >1 |
| 3 | 3 | 1.0 | none | 120 | 8 |
| 4 | 3 | 4.0 | none | 150 | 10 |
| 5 | 3 | 7.0 | none | 68 | 5 |
| 6 | 3 | 4.0 | NaOH (0.3) | 848 | 58 |
| 7 | 3 | 4.0 | NaOH (0.5) | 1223 | 84 |
| 8 | 3 | 4.0 | NaOH (0.75) | 1204 | 83 |
| 9 | 3 | 4.0 | NaOH (1.0) | 1170 | 80 |

Example 35

Method for Generating Hydrogen from Methanol and Water (Consecutive Addition Method)

[Formula 17]

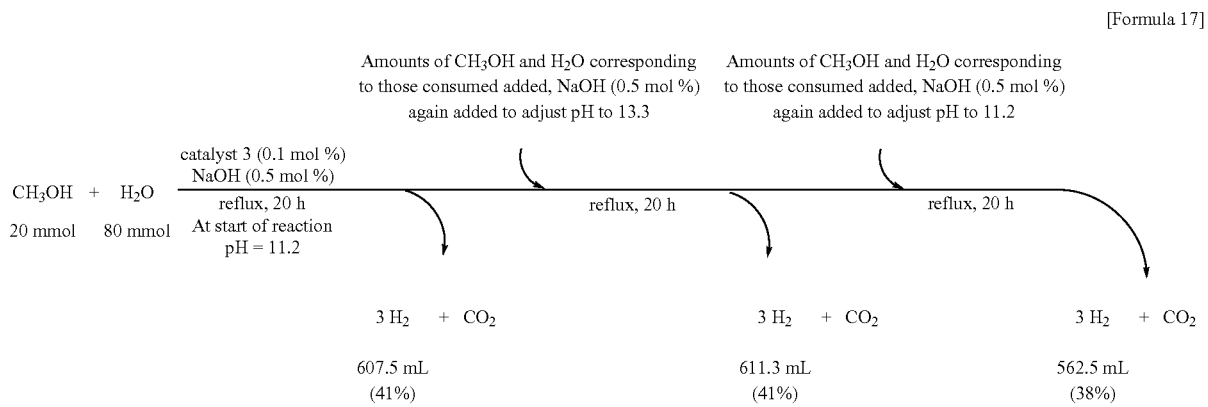

The construction of a catalyst system for continuously generating hydrogen from mixture of methanol and water was examined.

First, catalyst 3 (0.1 mol %) and sodium hydroxide (0.5 mol %) were added to a mixture of methanol (20 mmol) and water (80 mmol). At this point, the pH of the system was 11.2. When a reaction of this mixture was carried out under reflux conditions for 20 hours, 607.5 mL (yield 41%) of hydrogen was generated. Here, amounts of methanol (8.2 mmol) and water (8.2 mmol) corresponding to those consumed were added to the reaction system, sodium hydroxide (0.5 mol %) was again added to thus adjust the pH of the system to 11.3, and a reaction was then carried out under reflux conditions for 20 hours, and 611.3 mL (yield 41%) of hydrogen was generated. By repeating the same procedure, 562.5 mL (yield 38%) of hydrogen could be obtained.

By such a continuous method for generating hydrogen, a total of 1781.3 mL (71.5 mmol) of hydrogen could be obtained, and a catalytic turnover number of 1191 was achieved. In accordance with a procedure of continuously adding starting materials (mixture of methanol and water) that are safe and easy to handle and sodium hydroxide to the catalyst and heating, a new system that can continuously generate hydrogen gas can be developed.

Example 36

Method for Generating Hydrogen from Methanol and Water (Continuous Addition Method No. 1)

[Formula 18]

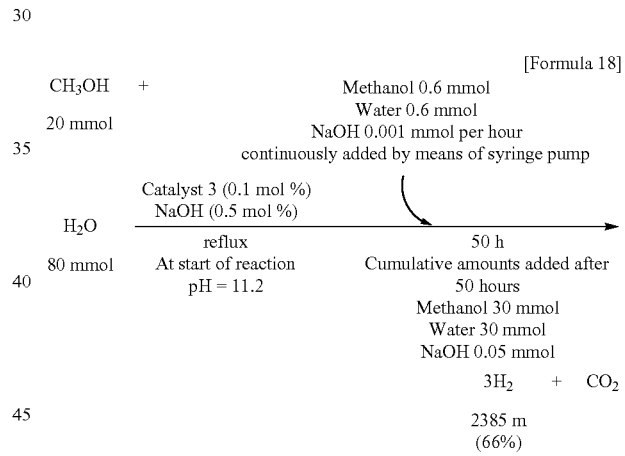

In order to replenish the amounts of methanol and water that had been consumed accompanying catalytic generation of hydrogen, an experiment involving addition at a constant rate using a syringe pump was carried out.

First, catalyst 3 (0.1 mol %) and sodium hydroxide (0.5 mol %) were added to a mixture of methanol (20 mmol) and water (80 mmol). At this point, the pH of the system was 11.2. Refluxing of the reaction system was started by heating, and a premixed solution [methanol (0.6 mmol/h), water (0.6 mmol/h), sodium hydroxide (0.001 mmol/h)] was added using a syringe pump. The generation of gas at a substantially constant rate was observed by continuing refluxing; after 50 hours 2385 mL of hydrogen (99.61 mmol) could be obtained, and a catalytic turnover number of 1660 was achieved.

In accordance with such a continuous reaction by replenishing consumed starting materials (methanol and water) and sodium hydroxide at amounts corresponding to the consumption rates, hydrogen gas can be generated continuously at a substantially constant rate over a long period of time (50 hours).

Example 37

Method for Generating Hydrogen from Methanol and Water (Continuous Addition Method No. 2)

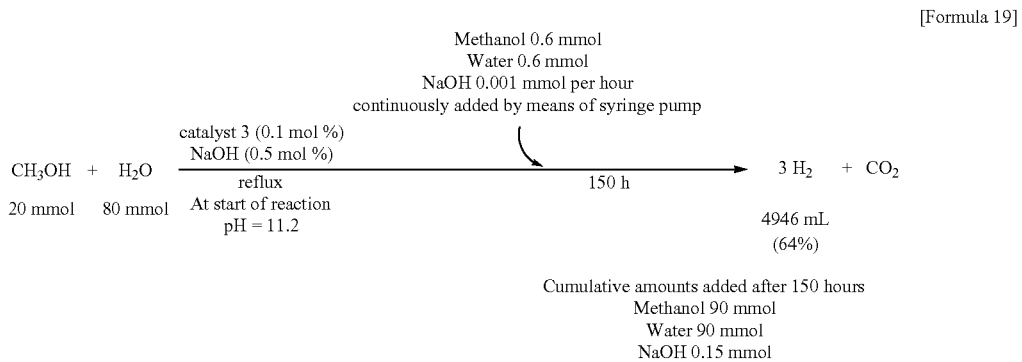

[Formula 19]

In order to replenish the amounts of methanol and water that had been consumed accompanying catalytic generation of hydrogen, an experiment involving addition at a constant rate using a syringe pump was similarly carried out for an extended period of 150 hours.

First, catalyst 3 (0.1 mol %) and sodium hydroxide (0.5 mol %) were added to a mixture of methanol (20 mmol) and water (80 mmol). At this point, the pH of the system was 11.2. Refluxing of the reaction system was started by heating, and a premixed solution [methanol (0.6 mmol/h), water (0.6 mmol/h), sodium hydroxide (0.001 mmol/h)] was added using a syringe pump. The generation of gas at a substantially constant rate was observed by continuing refluxing; after 150 hours 4946 mL of hydrogen (210.2 mmol) could be obtained, and a catalytic turnover number of 3502 was achieved.

In accordance with such a continuous reaction by replenishing the consumed starting materials (methanol and water) and sodium hydroxide at amounts corresponding to the consumption rates, hydrogen gas can be generated continuously at a substantially constant rate over a long period of time (150 hours).

Example 38

Dehydrogenative Synthesis Reaction for Carboxylic Acid from Lower Alcohol and Water as Starting Materials A catalytic reaction for obtaining hydrogen at the same time as obtaining, using a mixture of a lower alcohol (ethanol, 1-propanol, 1-butanol) and water as starting materials, a carboxylic acid having the corresponding number of carbons was examined. First, anionic catalyst 3 (3.0 mol %) and sodium hydroxide (3.0 mol %) were added to a mixture of ethanol (10 mmol) and water (20 mmol), and when a reaction was carried out under reflux conditions for 20 hours acetic acid was formed at a yield of 85%, and 445 mL (yield 92%) of hydrogen was also obtained (entry 1). When a similar reaction using a mixture of 1-propanol and water as starting materials was carried out over 40 hours, propionic acid was obtained at a yield of 68%, and 411 mL (yield 85%) of hydrogen was also generated. In this reaction, a small amount (18%) of an ester product (propyl propionate) was also observed (entry 2). Furthermore, when a reaction using a mixture of 1-butanol and water as starting materials was carried out, a similar carboxylic acid formation reaction progressed, and butyric acid could be obtained accompanied by the generation of hydrogen (entries 3 and 4).

TABLE 7

$$R\text{—}OH + H_2O \xrightarrow[\text{Reflux}]{\text{Catalyst 3 (3.0 mol \%)} \atop \text{NaOH (3.0 mol \%)}} R\text{—}C(=O)\text{—}OH + 2 H_2$$

10 mmol    20 mmol

| entry | Alcohol | Time (h) | Volume of hydrogen generated (mL) | Yield of hydrogen (%) | Yield of carboxylic acid (%) |
|---|---|---|---|---|---|
| 1 | Ethanol | 20 | 445 | 92 | 85 |
| 2 | 1-Propanol | 40 | 411 | 85 | 68[a] |
| 3 | 1-Butanol | 20 | 411 | 85 | 60[b] |
| 4 | 1-Butanol | 40 | 422 | 87 | 70[c] |

[a]Ester (propyl propionate) also formed at a yield of 18%.
[b]Ester (butyl butyrate) also formed at a yield of 30%.
[c]Ester (butyl butyrate) also formed at a yield of 22%.

The invention claimed is:

1. An organometallic compound of Formula (2)

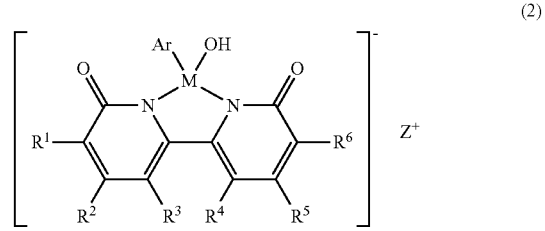

(2)

Wherein

Ar is an optionally substituted benzene or an optionally substituted cyclopentadienyl group, M is ruthenium, rhodium, or iridium, $R^1$ to $R^6$ are mutually independently a hydrogen atom, a halogen atom, a nitro group, a cyano group, a hydroxy group, a sulfo group, a mercapto group, a carboxyl group, or a C1-10 alkyl group, C3-15 cycloalkyl group, C6-15 aryl group, C1-10 heterocyclyl group, C2-10 alkenyl group, C2-10 alkynyl group, a C1-10 alkoxy group, a C1-10 ester group, C1-10 fluoroalkyl group, C1-10 acyl group, C1-10 sulfonyl group, C1-10 amino group, C1-10 amide group, C1-10 sulfenyl group, or C1-10 silyl group in which one or more hydrogen atoms are optionally substituted, $R^3$ and $R^4$ are optionally bonded to each other to form —CH=CH—, the hydrogens in the —CH=CH— are optionally substituted independently by a halogen atom, a nitro group, a cyano group, a hydroxy group, a sulfo group, a mercapto group, a carboxyl group, or a C1-10 alkyl group, C3-15 cycloalkyl group, C6-15 aryl group, C1-10 heterocyclyl group, C2-10 alkenyl group, C2-10 alkynyl group, C1-10 alkoxy group, C1-10 ester group, C1-10 fluoroalkyl group, C1-10 acyl group, C1-10 sulfonyl group, C1-10 amino group, C1-10 amide group, C1-10 sulfenyl group, or C1-10 silyl group, in which one or more hydrogen atoms are optionally substituted, and Z is Na, Li, K, or Cs.

2. The organometallic compound according to claim 1, wherein Ar is an optionally substituted cyclopentadienyl group, and M is iridium.

3. A method for dehydrogenating an oxygen-containing compound, the method comprising reacting use of a catalyst containing the organometallic compound according to claim 1 with an oxygen-containing compund to produce a carbonyl compund or an unsaturated bond-containing compound, and hydrogen ($H_2$).

4. The method according to claim 3, wherein the oxygen-containing compound is an alcohol, formic acid, or a formate.

5. A method for producing hydrogen ($H_2$), the method comprising reacting an alcohol, a mixture of an alcohol and water, formic acid, or a formate with a catalyst containing the organometallic compound according to claim 1 to produce hydrogen ($H_2$).

6. A method for producing a carbonyl compound, the method comprising reacting a catalyst containing the organometallic compound according to claim 1 with an alcohol to produce a corresponding carbonyl compound and hydrogen ($H_2$).

7. The method according to claim 6, wherein the carbonyl compound is a ketone or an aldehyde.

8. The method according to claim 6, wherein the alcohol is a primary alcohol, the carbonyl compound is a carboxylic acid, and a solvent comprising water is used.

9. A method for continuously producing hydrogen ($H_2$), the method comprising adding an alkaline compound to a mixture containing an alcohol and water, carrying out a dehydrogenation reaction in the presence of an organometallic compound one of Formula (2) according to claim 1, and adding said mixture and said alkaline compound one or more times in the course of progress of dehydrogenation, to produce hydrogen ($H_2$).

10. A dehydrogenation catalyst comprising the organometallic compound according to claim 1.

* * * * *